US008871905B2

(12) United States Patent
Holmes et al.

(10) Patent No.: US 8,871,905 B2
(45) Date of Patent: Oct. 28, 2014

(54) MODIFICATION OF CXCR4 USING ENGINEERED ZINC FINGER PROTEINS

(75) Inventors: Michael C. Holmes, Oakland, CA (US); Jeffrey C. Miller, San Leandro, CA (US); Jianbin Wang, San Ramon, CA (US)

(73) Assignee: Sangamo BioSciences, Inc., Richmond, CA (US)

( * ) Notice: Subject to any disclaimer, the term of this patent is extended or adjusted under 35 U.S.C. 154(b) by 660 days.

(21) Appl. No.: 12/661,539

(22) Filed: Mar. 18, 2010

(65) Prior Publication Data
US 2010/0291048 A1 Nov. 18, 2010

Related U.S. Application Data

(60) Provisional application No. 61/210,636, filed on Mar. 20, 2009, provisional application No. 61/273,861, filed on Aug. 10, 2009.

(51) Int. Cl.
| C12N 15/00 | (2006.01) |
| C12N 15/62 | (2006.01) |
| A61K 38/00 | (2006.01) |
| C07K 14/705 | (2006.01) |
| C07K 14/715 | (2006.01) |

(52) U.S. Cl.
CPC ......... *C07K 14/7158* (2013.01); *C07K 2319/81* (2013.01); *C07K 14/70596* (2013.01)
USPC ......... 530/350; 424/93.2; 424/94.1; 435/455; 435/462; 514/44; 536/23.4

(58) Field of Classification Search
USPC ........... 424/93.2, 94.1; 435/455, 462; 514/44; 530/350; 536/23.4
See application file for complete search history.

(56) References Cited

U.S. PATENT DOCUMENTS

| 5,356,802 A | 10/1994 | Chandrasegaran |
| 5,487,994 A | 1/1996 | Chandrasegaran |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas |
| 6,140,466 A | 10/2000 | Barbas et al. |
| 6,200,759 B1 | 3/2001 | Dove et al. |
| 6,242,568 B1 | 6/2001 | Barbas et al. |
| 6,410,248 B1 | 6/2002 | Greisman et al. |
| 6,453,242 B1 | 9/2002 | Eisenberg et al. |
| 6,503,717 B2 | 1/2003 | Case et al. |
| 6,534,261 B1 | 3/2003 | Cox et al. |
| 6,599,692 B1 | 7/2003 | Case et al. |
| 6,607,882 B1 | 8/2003 | Cox et al. |
| 6,824,978 B1 | 11/2004 | Cox et al. |
| 6,933,113 B2 | 8/2005 | Case et al. |
| 6,979,539 B2 | 12/2005 | Cox et al. |
| 7,013,219 B2 | 3/2006 | Case et al. |
| 7,163,824 B2 | 1/2007 | Cox et al. |
| 2002/0160940 A1 | 10/2002 | Case et al. |
| 2003/0068675 A1* | 4/2003 | Liu .............................. 435/69.1 |
| 2003/0232410 A1 | 12/2003 | Liljedahl et al. |
| 2005/0026157 A1 | 2/2005 | Baltimore et al. |
| 2005/0064474 A1 | 3/2005 | Urnov et al. |
| 2005/0208489 A1 | 9/2005 | Carroll et al. |
| 2006/0188987 A1 | 8/2006 | Guschan et al. |
| 2007/0134796 A1 | 6/2007 | Holmes et al. |
| 2007/0218528 A1 | 9/2007 | Miller et al. |
| 2008/0015164 A1 | 1/2008 | Collingwood |
| 2008/0131962 A1 | 6/2008 | Miller |
| 2008/0159996 A1 | 7/2008 | Ando et al. |
| 2008/0188000 A1* | 8/2008 | Reik et al. ..................... 435/463 |
| 2010/0003756 A1* | 1/2010 | Collingwood et al. ........ 435/455 |
| 2010/0199389 A1* | 8/2010 | Butler et al. .................. 800/298 |

FOREIGN PATENT DOCUMENTS

| GB | 2338237 A | 12/1999 |
| WO | WO 95/19431 A1 | 7/1995 |
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/16536 A1 | 2/2002 |

(Continued)

OTHER PUBLICATIONS

Abraham, et al., "The CXCR4 Antagonist 4F-Benzoyl-TN14003 Stimulates the Recovery of the Bone Marrow After Transplantation," *Leukemia* 23:1378-1388 (2009).
Beerli, et al., "Engineering Polydactyl Zinc-Finger Transcription Factors," *Nature Biotechnology* 20:135-141 (2002).
Bitinate, et al., "FOKI Dimerization Is Required for DNA Cleavage," *PNAS USA* 95:10570-10575 (1998).
Choo, et al., "Advances in Zinc Finger Engineering," *Curr. Opin. Struct. Biol.* 10:411-416 (2000).
Connor, et al., "Change in Co-Receptor Use Correlates With Disease Progression in HIV-1 Infected Individuals," *J Exp Med* 185:621-628 (1997).
Deng, et al. "Identification of a Major Co-Receptor for Primary Isolates of HIV-1," *Nature* 381:661-666(1996).

(Continued)

*Primary Examiner* — Kevin Hill
(74) *Attorney, Agent, or Firm* — Pasternak Patent Law; Susan Abrahamson

(57) ABSTRACT

Disclosed herein are methods and compositions for modulating activity of CXCR4 genes, for example using zinc finger transcription factors (ZF-TFs) or zinc finger nucleases (ZFNs) comprising a zinc finger protein and a cleavage domain or cleavage half-domain. Polynucleotides encoding ZF-TFs or ZFNs, vectors comprising polynucleotides encoding ZF-TFs or ZFNs and cells comprising polynucleotides encoding ZF-TFs or ZFNs and/or cells comprising ZF-TF or ZFNs are also provided.

19 Claims, 13 Drawing Sheets

(56) References Cited

FOREIGN PATENT DOCUMENTS

| WO | WO 02/057308 A2 | 7/2002 |
|---|---|---|
| WO | WO 02/077227 A2 | 10/2002 |
| WO | WO 02/099084 A2 | 12/2002 |
| WO | WO 03/016496 A2 | 2/2003 |
| WO | WO 2006/126209 A1 | 11/2006 |
| WO | WO 2007/014275 A2 | 1/2007 |
| WO | WO 2007/139982 A2 | 12/2007 |

OTHER PUBLICATIONS

Feng, et al., "HIV-1 Entry Cofactor: Functional CDNA Cloning of a Seven-Transmembrane, G Protein-Coupled Receptor," *Science* 272:872-877 (1996).

Flomenberg, et al., "Role of CXCR4 Chemokine Receptor Blockade Using AMD3100 for Mobilization of Autologous Hematopoietic Progenitor Cells," *Acta Haematol* 114:198-205 (2005).

Isalan et al., "A Rapid, Generally Applicable Method to Engineer Zinc Fingers Illustrated by Targeting the HIV-1 Promoter," *Nat Biotechnol* 19:656-660 (2001).

Karlsson, et al., "MT-2 Cell Tropism As Prognostic Marker for Disease Progression in Human Immunodeficiency Virus Type 1 Infection," *J. Clin Microbiol* 32:364-370 (1994).

Kim, et al., "Chimeric Restriction Endonuclease," *PNAS USA* 91:883-887 (1994).

Kim, et al., "Insertion and Deletion Mutants of FOKI Restriction Endonuclease,"*J. Biol. Chem.* 269:31978-31981 (1994).

Li, et al., "Functional Domains in FOK I Restriction Endonuclease," *PNAS USA* 89:4275-4279 (1992).

Li, et al., "Alteration of the Cleavage Distance of FOK I Restriction Endonuclease by Insertion Mutagenesis," *PNAS USA* 90:2764-2768 (1993).

Miller, et al., "An Improved Zinc-Finger Nuclease Architecture for Highly Specific Genome Editing," *Nature Biotech* 25:778-785 (2007).

Pabo, et al., "Design and Selection of Novel CYS2-HIS2 Zinc Finger Proteins," *Ann. Rev. Biochem.* 70:313-340 (2001).

Perez, et at., "Establishment of HIV-1 Resistance in CD4+ T Cells by Genome Editing Using Zinc-Finger Nucleases," *Nature Biotechnology* 26:808-816 (2008).

Richman, et al., "The Impact of the Syncytium-Inducing Phenotype of Human Immunodeficiency Virus on Disease Progression," *J Infect Dis* 169:968-974 (1994).

Santiago, et al., "Targeted Gene Knockout in Mammalian Cells by Using Engineered Zinc Finger Nucleases," *PNAS USA* 105:5809-5814 (2008).

Schenten, et al., "Effects of Soluble CD4 on Simian Immunodeficiency Virus Infection of CD4-Positive and CD4-Negative Cells," *J Virol* 73:5373-5380 (1999).

Schuitemaker, et al., "Biological Phenotype of Human Immunodeficiency Virus Type 1 Clones At Different Stages of Infection: Progression of Disease Is Associated With a Shift From Monocytotropic to T-Cell-Tropic Virus Population," *J Virol* 66:1354-1360 (1992).

Segal, et al., "Custom DNA-Binding Proteins Come of Age: Polydactyl Zinc-Finger Proteins," *Curr. Opin. Biotechnol.* 12:632-637 (2001).

Szczpek, et al., "Structure-Based Redesign of the Dimerization Interface Reduces the Toxicity of Zinc-Finger Nucleases," *Nat Biotechnol* 25:786-793 (2007).

Umov, et al., "Highly Efficient Endogenous Human Gene Correction Using Designed Zinc-Finger Nucleases" *Nature* 435:646-651 (2005).

Vandercappellen, et al., "The Role of CXC Chemokines and Their Receptors in Cancer," *Cancer Lett* 28:226-244 (2008).

Van't Wout, et al., "Macrophage-Tropic Variants Initiate Human Immunodeficiency Virus Type 1 Infection After Sexual, Parenteral, and Vertical Transmission," *J Clin Invest* 94:2060-2067 (1994).

U.S. Appl. No. 61/337,769, filed Feb. 8, 2010 entitled "Engineered Cleavage Half-Domains" by Doyon et al.

Mani, et al. "Design, Engineering, and Characterization of Zinc Finger Nucleases," *Biochemical and Biophysical Research Communications* 335:447-457 (2005).

Swan, et al., "Can Gene Delivery Close the Door to HIV-1 Entry After Escape?" *Journal of Medical Primatology* 35:236-247 (2006).

Wilen, et al., "Engineering HIV-Resistant Human CD4+T Cells With CXCR4-Specific Zinc-Finger Nucleases," *PLoS Pathogens* 7:1-15 (2011).

* cited by examiner

Fig. 1A

5'-GTGACCGGCTTCTACCCCAATGACTTGTGGGTGGT-3'
3'-CACTGGCGAAGATGGGGTTACTGAACACCCACCA-5'
                    12273           12270

|  | GAC | TTG | TGG | GTG |
|--|-----|-----|-----|-----|
| 12270 | DRSNLTR | RSDSLSA | RSDHLTT | RSDSLLR |

|  | GTA | GAA | GCG | GTC |
|--|-----|-----|-----|-----|
| 12273 | QSGSLTR | QSGNLAR | RSDDLTR | DRSALSR |

Fig. 1B

5'-CACGCTTCCCTTCTGGGCAGTTGATGCCGTGGC-3'
3'-GTGCGAAGGGAAGACCCGTCAACTACGGCACCG-5'
                    12290

|  | GTT | GAT | GCC | GTG |
|--|-----|-----|-----|-----|
| 12281 | TSGSLTR | TSGNLTR | DRSDLSR | RSDALSR |

|  | AGA | AGG | GAA | GCG |
|--|-----|-----|-----|-----|
| 12290 | QSAHRIT | RSDHLSA | QSGNLAR | RSDDLTR |

Fig. 1C

5'-CCATCGTCCAGCGCCACCAACAGTCAGAGGCCAAGGA-3'
3'-GGTAGCAGGTGCGGTGGTTGTCAGTCTCCGGTTCCT-5'
                    12329

|  | TCA | GAG | GCC | AAG |
|--|-----|-----|-----|-----|
| 12257 | QSADRTK | RSDNLAR | DNSTRIK | RSDTLSV |

|  | GGT | GGC | GTG | GAC | GAT |
|--|-----|-----|-----|-----|-----|
| 12329 | TSGHLSR | DRSHLSR | RSDALAR | DRSNLTR | TSGNLTR |

Figure 2B

```
WT:       GTGACCGCTTCTACCCCAATGACTTGTGGGTGGT
A66-seq1: GTGACCGCTTCTACCCC--T--C-TGTGGGTGGT
A66-seq2: GTGACCGCTTCT-------GACTTGTGGGTGGT
```

Figure 2C

```
WT:      ATATCTGTGACCGCTTCTACCCCAATGACTTGTGGGTGGT
B4-seq1: ATATCTGTGACCGCTTCTACCC---------GGTGGT
B4-seq2: ATATCT-----------------TGACTTGTGGGTGGT
```

Figure 2D

```
WT:       AGGCAGATGACAGATATATCTGTGACCGCTTCTACCCCAATGACTTGTGGG
TGGTTGTGTTCCAGTTTCAGCA
B13-seq1: AGGCAGATGACAGATATATCTGTGACCGCTTCTACC--------TGTGGG
TGGTTGTGTTCCAGTTTC
B13-seq2: AGGCAGATGACAGATATATCTG----------------------------
TGGTTGTGTTCCAGTTTC
B13-seq3: AGGCAG--------------------------------------------
--------TCCAGTTTC
```

```
                         SEQUENCE LISTING

<160> NUMBER OF SEQ ID NOS: 52

<210> SEQ ID NO 1
<211> LENGTH: 28
<212> TYPE: DNA
<213> ORGANISM: Homo sapiens
<220> FEATURE:
<221> NAME/KEY: misc_feature
<223> OTHER INFORMATION: target site of the CXCR4 zinc-finger

<400> SEQUENCE: 1
atgacttgtg ggtggttgtg ttccagtt                                       28

<210> SEQ ID NO 2
<211> LENGTH: 7
<212> TYPE: PRT
<213> ORGANISM: Artificial Sequence
<220> FEATURE:
<223> OTHER INFORMATION: Chemically synthesized zinc finger protein

<400> SEQUENCE: 2

Arg Ser Asp Ser Leu Leu Arg
1               5

<210> SEQ ID NO 3
<211> LENGTH: 7
<212> TYPE: PRT
<213> ORGANISM: Artificial Sequence
<220> FEATURE:
<223> OTHER INFORMATION: Chemically synthesized zinc finger protein

<400> SEQUENCE: 3

Arg Ser Asp His Leu Thr Thr
1               5

<210> SEQ ID NO 4
<211> LENGTH: 7
<212> TYPE: PRT
<213> ORGANISM: Artificial Sequence
<220> FEATURE:
<223> OTHER INFORMATION: Chemically synthesized zinc finger protein

<400> SEQUENCE: 4

Arg Ser Asp Ser Leu Ser Ala
1               5

<210> SEQ ID NO 5
<211> LENGTH: 7
<212> TYPE: PRT
<213> ORGANISM: Artificial Sequence
<220> FEATURE:
<223> OTHER INFORMATION: Chemically synthesized zinc finger protein

<400> SEQUENCE: 5

Asp Arg Ser Asn Leu Thr Arg
1               5

<210> SEQ ID NO 6
<211> LENGTH: 28
<212> TYPE: DNA
<213> ORGANISM: Homo sapiens
<220> FEATURE:
<221> NAME/KEY: misc_feature
```

```
<223> OTHER INFORMATION: target site of the CXCR4 zinc-finger

<400> SEQUENCE: 6
gggtagaagc ggtcacagat atatctgt                                              28

<210> SEQ ID NO 7
<211> LENGTH: 7
<212> TYPE: PRT
<213> ORGANISM: Artificial Sequence
<220> FEATURE:
<223> OTHER INFORMATION: Chemically synthesized zinc finger protein

<400> SEQUENCE: 7

Asp Arg Ser Ala Leu Ser Arg
1               5

<210> SEQ ID NO 8
<211> LENGTH: 7
<212> TYPE: PRT
<213> ORGANISM: Artificial Sequence
<220> FEATURE:
<223> OTHER INFORMATION: Chemically synthesized zinc finger protein

<400> SEQUENCE: 8

Arg Ser Asp Asp Leu Thr Arg
1               5

<210> SEQ ID NO 9
<211> LENGTH: 7
<212> TYPE: PRT
<213> ORGANISM: Artificial Sequence
<220> FEATURE:
<223> OTHER INFORMATION: Chemically synthesized zinc finger protein

<400> SEQUENCE: 9

Gln Ser Gly Asn Leu Ala Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Chemically synthesized zinc finger protein

<400> SEQUENCE: 10

Gln Ser Gly Ser Leu Thr Arg
1               5

<210> SEQ ID NO 11
<211> LENGTH: 28
<212> TYPE: DNA
<213> ORGANISM: Homo sapiens
<220> FEATURE:
<221> NAME/KEY: misc_feature
<223> OTHER INFORMATION: target site of the CXCR4 zinc-finger

<400> SEQUENCE: 11
agtcagaggc caaggaagct gttggctg                                              28

<210> SEQ ID NO 12
<211> LENGTH: 7
<212> TYPE: PRT
<213> ORGANISM: Artificial Sequence
<220> FEATURE:
<223> OTHER INFORMATION: Chemically synthesized zinc finger protein
```

-continued

<400> SEQUENCE: 12

Arg Ser Asp Thr Leu Ser Val
1               5

<210> SEQ ID NO 13
<211> LENGTH: 7
<212> TYPE: PRT
<213> ORGANISM: Artificial Sequence
<220> FEATURE:
<223> OTHER INFORMATION: Chemically synthesized zinc finger protein

<400> SEQUENCE: 13

Asp Asn Ser Thr Arg Ile Lys
1               5

<210> SEQ ID NO 14
<211> LENGTH: 7
<212> TYPE: PRT
<213> ORGANISM: Artificial Sequence
<220> FEATURE:
<223> OTHER INFORMATION: Chemically synthesized zinc finger protein

<400> SEQUENCE: 14

Arg Ser Asp Asn Leu Ala Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Chemically synthesized zinc finger protein

<400> SEQUENCE: 15

Gln Ser Ala Asp Arg Thr Lys
1               5

<210> SEQ ID NO 16
<211> LENGTH: 28
<212> TYPE: DNA
<213> ORGANISM: Homo sapiens
<220> FEATURE:
<221> NAME/KEY: misc_feature
<223> OTHER INFORMATION: target site of the CXCR4 zinc-finger

<400> SEQUENCE: 16
ttggtggcgt ggacgatggc caggtagc                                    28

<210> SEQ ID NO 17
<211> LENGTH: 7
<212> TYPE: PRT
<213> ORGANISM: Artificial Sequence
<220> FEATURE:
<223> OTHER INFORMATION: Chemically synthesized zinc finger protein

<400> SEQUENCE: 17

Thr Ser Gly Asn Leu Thr Arg
1               5

<210> SEQ ID NO 18
<211> LENGTH: 7
<212> TYPE: PRT
<213> ORGANISM: Artificial Sequence
<220> FEATURE:
<223> OTHER INFORMATION: Chemically synthesized zinc finger protein

<400> SEQUENCE: 18

Arg Ser Asp Ala Leu Ala Arg
1               5

<210> SEQ ID NO 19
<211> LENGTH: 7
<212> TYPE: PRT
<213> ORGANISM: Artificial Sequence
<220> FEATURE:
<223> OTHER INFORMATION: Chemically synthesized zinc finger protein

<400> SEQUENCE: 19

Asp Arg Ser His Leu Ser Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Chemically synthesized zinc finger protein

<400> SEQUENCE: 20

Thr Ser Gly His Leu Ser Arg
1               5

<210> SEQ ID NO 21
<211> LENGTH: 28
<212> TYPE: DNA
<213> ORGANISM: Homo sapiens
<220> FEATURE:
<221> NAME/KEY: misc_feature
<223> OTHER INFORMATION: target site of the CXCR4 zinc-finger

<400> SEQUENCE: 21
cagttgatgc cgtggcaaac tggtactt                                          28

<210> SEQ ID NO 22
<211> LENGTH: 7
<212> TYPE: PRT
<213> ORGANISM: Artificial Sequence
<220> FEATURE:
<223> OTHER INFORMATION: Chemically synthesized zinc finger protein

<400> SEQUENCE: 22

Arg Ser Asp Ala Leu Ser Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Chemically synthesized zinc finger protein

<400> SEQUENCE: 23

Asp Arg Ser Asp Leu Ser Arg
1               5

<210> SEQ ID NO 24
<211> LENGTH: 7
<212> TYPE: PRT
<213> ORGANISM: Artificial Sequence
<220> FEATURE:
<223> OTHER INFORMATION: Chemically synthesized zinc finger protein

<400> SEQUENCE: 24

```
Thr Ser Gly Ser Leu Thr Arg
 1               5
```

<210> SEQ ID NO 25
<211> LENGTH: 28
<212> TYPE: DNA
<213> ORGANISM: Homo sapiens
<220> FEATURE:
<221> NAME/KEY: misc_feature
<223> OTHER INFORMATION: target site of the CXCR4 zinc-finger

<400> SEQUENCE: 25
ccagaaggga agcgtgatga caaagagg                                          28

<210> SEQ ID NO 26
<211> LENGTH: 7
<212> TYPE: PRT
<213> ORGANISM: Artificial Sequence
<220> FEATURE:
<223> OTHER INFORMATION: Chemically synthesized zinc finger protein

<400> SEQUENCE: 26

```
Arg Ser Asp His Leu Ser Ala
 1               5
```

<210> SEQ ID NO 27
<211> LENGTH: 7
<212> TYPE: PRT
<213> ORGANISM: Artificial Sequence
<220> FEATURE:
<223> OTHER INFORMATION: Chemically synthesized zinc finger protein

<400> SEQUENCE: 27

```
Gln Ser Ala His Arg Ile Thr
 1               5
```

<210> SEQ ID NO 28
<211> LENGTH: 352
<212> TYPE: PRT
<213> ORGANISM: Homo sapiens
<220> FEATURE:
<221> NAME/KEY: misc_feature
<223> OTHER INFORMATION: CXCR4 isoform b, WT

<400> SEQUENCE: 28

```
Met Glu Gly Ile Ser Ile Tyr Thr Ser Asp Asn Tyr Thr Glu Glu Met
 1               5                  10                  15

Gly Ser Gly Asp Tyr Asp Ser Met Lys Glu Pro Cys Phe Arg Glu Glu
             20                  25                  30

Asn Ala Asn Phe Asn Lys Ile Phe Leu Pro Thr Ile Tyr Ser Ile Ile
         35                  40                  45

Phe Leu Thr Gly Ile Val Gly Asn Gly Leu Val Ile Leu Val Met Gly
     50                  55                  60

Tyr Gln Lys Lys Leu Arg Ser Met Thr Asp Lys Tyr Arg Leu His Leu
 65                  70                  75                  80

Ser Val Ala Asp Leu Leu Phe Val Ile Thr Leu Pro Phe Trp Ala Val
                 85                  90                  95

Asp Ala Val Ala Asn Trp Tyr Phe Gly Asn Phe Leu Cys Lys Ala Val
            100                 105                 110

His Val Ile Tyr Thr Val Asn Leu Tyr Ser Ser Val Leu Ile Leu Ala
        115                 120                 125

Phe Ile Ser Leu Asp Arg Tyr Leu Ala Ile Val His Ala Thr Asn Ser
    130                 135                 140
```

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
            165                 170                 175

Val Ser Glu Ala Asp Asp Arg Tyr Ile Cys Asp Arg Phe Tyr Pro Asn
        180                 185                 190

Asp Leu Trp Val Val Val Phe Gln Phe Gln His Ile Met Val Gly Leu
            195                 200                 205

Ile Leu Pro Gly Ile Val Ile Leu Ser Cys Tyr Cys Ile Ile Ile Ser
        210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
            245                 250                 255

Ile Gly Ile Ser Ile Asp Ser Phe Ile Leu Leu Glu Ile Ile Lys Gln
        260                 265                 270

Gly Cys Glu Phe Glu Asn Thr Val His Lys Trp Ile Ser Ile Thr Glu
            275                 280                 285

Ala Leu Ala Phe Phe His Cys Cys Leu Asn Pro Ile Leu Tyr Ala Phe
        290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
            325                 330                 335

His Ser Ser Val Ser Thr Glu Ser Glu Ser Ser Ser Phe His Ser Ser
            340                 345                 350

<210> SEQ ID NO 29
<211> LENGTH: 272
<212> TYPE: PRT
<213> ORGANISM: Artificial Sequence
<220> FEATURE:
<223> OTHER INFORMATION: Synthetic clone #A66-seq1: 7 bp deletion and 2
      bp insertion

<400> SEQUENCE: 29

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Ile Phe Leu Pro Thr Ile Tyr Ser Ile Ile
        35                  40                  45

Phe Leu Thr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
            85                  90                  95

Asp Ala Val Ala Asn Trp Tyr Phe Gly Asn Phe Leu Cys Lys Ala Val
        100                 105                 110

His Val Ile Tyr Thr Val Asn Leu Tyr Ser Ser Val Leu Ile Leu Ala
        115                 120                 125

Phe Ile Ser Leu Asp Arg Tyr Leu Ala Ile Val His Ala Thr Asn Ser
    130                 135                 140

Gln Arg Pro Arg Lys Leu Leu Ala Glu Lys Val Val Tyr Val Gly Val

```
                145                 150                 155                 160
Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Ser
            180                 185                 190

Val Gly Gly Cys Val Pro Val Ser Ala His His Gly Trp Pro Tyr Pro
        195                 200                 205

Ala Trp Tyr Cys His Pro Val Leu Leu Leu His Tyr His Leu Gln Ala
    210                 215                 220

Val Thr Leu Gln Gly Pro Pro Glu Ala Gln Gly Pro Gln Asp His Ser
225                 230                 235                 240

His Pro His Pro Gly Phe Leu Arg Leu Leu Ala Ala Leu Leu His Trp
                245                 250                 255

Asp Gln His Arg Leu Leu His Pro Pro Gly Asn His Gln Ala Arg Val
                260                 265                 270

<210> SEQ ID NO 30
<211> LENGTH: 189
<212> TYPE: PRT
<213> ORGANISM: Artificial Sequence
<220> FEATURE:
<223> OTHER INFORMATION: Synthetic clone #A66-seq2: 8 bp deletion

<400> SEQUENCE: 30

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Ile Phe Leu Pro Thr Ile Tyr Ser Ile Ile
        35                  40                  45

Phe Leu Thr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
            100                 105                 110

His Val Ile Tyr Thr Val Asn Leu Tyr Ser Ser Val Leu Ile Leu Ala
        115                 120                 125

Phe Ile Ser Leu Asp Arg Tyr Leu Ala Ile Val His Ala Thr Asn Ser
    130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe
            180                 185

<210> SEQ ID NO 31
<211> LENGTH: 348
<212> TYPE: PRT
<213> ORGANISM: Artificial Sequence
<220> FEATURE:
<223> OTHER INFORMATION: Synthetic clone #B4-seq1: 12 bp deletion

<400> SEQUENCE: 31
```

```
Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Ile Phe Leu Pro Thr Ile Tyr Ser Ile Ile
                35                  40                  45

Phe Leu Thr Gly Ile Val Gly Asn Gly Leu Val Ile Leu Val Met Gly
50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
                100                 105                 110

His Val Ile Tyr Thr Val Asn Leu Tyr Ser Ser Val Leu Ile Leu Ala
            115                 120                 125

Phe Ile Ser Leu Asp Arg Tyr Leu Ala Ile Val His Ala Thr Asn Ser
130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Val
                180                 185                 190

Val Val Phe Gln Phe Gln His Ile Met Val Gly Leu Ile Leu Pro Gly
            195                 200                 205

Ile Val Ile Leu Ser Cys Tyr Cys Ile Ile Ser Lys Leu Ser His
            210                 215                 220

Ser Lys Gly His Gln Lys Arg Lys Ala Leu Lys Thr Thr Val Ile Leu
225                 230                 235                 240

Ile Leu Ala Phe Phe Ala Cys Trp Leu Pro Tyr Tyr Ile Gly Ile Ser
                245                 250                 255

Ile Asp Ser Phe Ile Leu Leu Glu Ile Ile Lys Gln Gly Cys Glu Phe
                260                 265                 270

Glu Asn Thr Val His Lys Trp Ile Ser Ile Thr Glu Ala Leu Ala Phe
            275                 280                 285

Phe His Cys Cys Leu Asn Pro Ile Leu Tyr Ala Phe Leu Gly Ala Lys
        290                 295                 300

Phe Lys Thr Ser Ala Gln His Ala Leu Thr Ser Val Ser Arg Gly Ser
305                 310                 315                 320

Ser Leu Lys Ile Leu Ser Lys Gly Lys Arg Gly Gly His Ser Ser Val
                325                 330                 335

Ser Thr Glu Ser Glu Ser Ser Ser Phe His Ser Ser
            340                 345

<210> SEQ ID NO 32
<211> LENGTH: 283
<212> TYPE: PRT
<213> ORGANISM: Artificial Sequence
<220> FEATURE:
<223> OTHER INFORMATION: Synthetic clone #B4-seq3: 19 bp deletion

<400> SEQUENCE: 32

Met Glu Gly Ile Ser Ile Tyr Thr Ser Asp Asn Tyr Thr Glu Glu Met
1               5                   10                  15
```

```
Gly Ser Gly Asp Tyr Asp Ser Met Lys Glu Pro Cys Phe Arg Glu Glu
            20                  25                  30

Asn Ala Asn Phe Asn Lys Ile Phe Leu Pro Thr Ile Tyr Ser Ile Ile
        35                  40                  45

Phe Leu Thr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
            85                  90                  95

Asp Ala Val Ala Asn Trp Tyr Phe Gly Asn Phe Leu Cys Lys Ala Val
            100                 105                 110

His Val Ile Tyr Thr Val Asn Leu Tyr Ser Ser Val Leu Ile Leu Ala
            115                 120                 125

Phe Ile Ser Leu Asp Arg Tyr Leu Ala Ile Val His Ala Thr Asn Ser
    130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Leu Thr Cys Gly Trp Leu Cys
            180                 185                 190

Ser Ser Phe Ser Thr Ser Trp Leu Ala Leu Ser Cys Leu Val Leu Ser
        195                 200                 205

Ser Cys Pro Ala Ile Ala Leu Ser Ser Pro Ser Cys His Thr Pro Arg
    210                 215                 220

Ala Thr Arg Ser Ala Arg Pro Ser Arg Pro Gln Ser Ser Ser Ser Trp
225                 230                 235                 240

Leu Ser Ser Pro Val Gly Cys Leu Thr Thr Leu Gly Ser Ala Ser Thr
                245                 250                 255

Pro Ser Ser Ser Trp Lys Ser Ser Lys Gly Val Ser Leu Arg Thr
            260                 265                 270

Leu Cys Thr Ser Gly Phe Pro Ser Pro Arg Pro
        275                 280

<210> SEQ ID NO 33
<211> LENGTH: 349
<212> TYPE: PRT
<213> ORGANISM: Artificial Sequence
<220> FEATURE:
<223> OTHER INFORMATION: Synthetic clone #B13: 9 bp deletion

<400> SEQUENCE: 33

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Ile Phe Leu Pro Thr Ile Tyr Ser Ile Ile
        35                  40                  45

Phe Leu Thr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
            85                  90                  95
```

Asp Ala Val Ala Asn Trp Tyr Phe Gly Asn Phe Leu Cys Lys Ala Val
            100                 105                 110

His Val Ile Tyr Thr Val Asn Leu Tyr Ser Val Leu Ile Leu Ala
    115                 120                 125

Phe Ile Ser Leu Asp Arg Tyr Leu Ala Ile Val His Ala Thr Asn Ser
130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Leu Trp
            180                 185                 190

Val Val Val Phe Gln Phe Gln His Ile Met Val Gly Leu Ile Leu Pro
            195                 200                 205

Gly Ile Val Ile Leu Ser Cys Tyr Cys Ile Ile Ile Ser Lys Leu Ser
            210                 215                 220

His Ser Lys Gly His Gln Lys Arg Lys Ala Leu Lys Thr Thr Val Ile
225                 230                 235                 240

Leu Ile Leu Ala Phe Phe Ala Cys Trp Leu Pro Tyr Tyr Ile Gly Ile
                245                 250                 255

Ser Ile Asp Ser Phe Ile Leu Leu Glu Ile Ile Lys Gln Gly Cys Glu
            260                 265                 270

Phe Glu Asn Thr Val His Lys Trp Ile Ser Ile Thr Glu Ala Leu Ala
            275                 280                 285

Phe Phe His Cys Cys Leu Asn Pro Ile Leu Tyr Ala Phe Leu Gly Ala
            290                 295                 300

Lys Phe Lys Thr Ser Ala Gln His Ala Leu Thr Ser Val Ser Arg Gly
305                 310                 315                 320

Ser Ser Leu Lys Ile Leu Ser Lys Gly Lys Arg Gly Gly His Ser Ser
                325                 330                 335

Val Ser Thr Glu Ser Glu Ser Ser Phe His Ser Ser
            340                 345

<210> SEQ ID NO 34
<211> LENGTH: 264
<212> TYPE: PRT
<213> ORGANISM: Artificial Sequence
<220> FEATURE:
<223> OTHER INFORMATION: Synthetic clone #B13-seq2: 29 bp deletion

<400> SEQUENCE: 34

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Ile Phe Leu Pro Thr Ile Tyr Ser Ile Ile
            35                  40                  45

Phe Leu Thr Gly Ile Val Gly Asn Gly Leu Val Ile Leu Val Met Gly
        50                  55                  60

Tyr Gln Lys Lys Leu Arg Ser Met Thr Asp Lys Tyr Arg Leu His Leu
65              70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
            100                 105                 110

```
His Val Ile Tyr Thr Val Asn Leu Tyr Ser Ser Val Leu Ile Leu Ala
            115                 120                 125

Phe Ile Ser Leu Asp Arg Tyr Leu Ala Ile Val His Ala Thr Asn Ser
        130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Gly Cys Val Pro Val Ser
            180                 185                 190

Ala His His Gly Trp Pro Tyr Pro Ala Trp Tyr Cys His Pro Val Leu
        195                 200                 205

Leu Leu His Tyr His Leu Gln Ala Val Thr Leu Gln Gly Pro Pro Glu
    210                 215                 220

Ala Gln Gly Pro Gln Asp His Ser His Pro His Pro Gly Phe Leu Arg
225                 230                 235                 240

Leu Leu Ala Ala Leu Leu His Trp Asp Gln His Arg Leu Leu His Pro
                245                 250                 255

Pro Gly Asn His Gln Ala Arg Val
            260

<210> SEQ ID NO 35
<211> LENGTH: 334
<212> TYPE: PRT
<213> ORGANISM: Artificial Sequence
<220> FEATURE:
<223> OTHER INFORMATION: Synthetic clone #B13-seq3: 54 bp deletion

<400> SEQUENCE: 35

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Ile Phe Leu Pro Thr Ile Tyr Ser Ile Ile
        35                  40                  45

Phe Leu Thr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
            100                 105                 110

His Val Ile Tyr Thr Val Asn Leu Tyr Ser Ser Val Leu Ile Leu Ala
            115                 120                 125

Phe Ile Ser Leu Asp Arg Tyr Leu Ala Ile Val His Ala Thr Asn Ser
        130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Val Gln Phe Gln His Ile Met Val Gly Leu Ile Leu
            180                 185                 190

Pro Gly Ile Val Ile Leu Ser Cys Tyr Cys Ile Ile Ser Lys Leu
        195                 200                 205
```

-continued

```
Ser His Ser Lys Gly His Gln Lys Arg Lys Ala Leu Lys Thr Thr Val
    210                 215                 220
Ile Leu Ile Leu Ala Phe Phe Ala Cys Trp Leu Pro Tyr Tyr Ile Gly
225                 230                 235                 240
Ile Ser Ile Asp Ser Phe Ile Leu Leu Glu Ile Ile Lys Gln Gly Cys
            245                 250                 255
Glu Phe Glu Asn Thr Val His Lys Trp Ile Ser Ile Thr Glu Ala Leu
        260                 265                 270
Ala Phe Phe His Cys Cys Leu Asn Pro Ile Leu Tyr Ala Phe Leu Gly
    275                 280                 285
Ala Lys Phe Lys Thr Ser Ala Gln His Ala Leu Thr Ser Val Ser Arg
    290                 295                 300
Gly Ser Ser Leu Lys Ile Leu Ser Lys Gly Lys Arg Gly Gly His Ser
305                 310                 315                 320
Ser Val Ser Thr Glu Ser Glu Ser Ser Ser Phe His Ser Ser
            325                 330
```

<210> SEQ ID NO 36
<211> LENGTH: 25
<212> TYPE: DNA
<213> ORGANISM: Artificial Sequence
<220> FEATURE:
<223> OTHER INFORMATION: Synthetic primer

<400> SEQUENCE: 36
caacctctac agcagtgtcc tcatc                                           25

<210> SEQ ID NO 37
<211> LENGTH: 22
<212> TYPE: DNA
<213> ORGANISM: Artificial Sequence
<220> FEATURE:
<223> OTHER INFORMATION: Synthetic primer

<400> SEQUENCE: 37
ggagtgtgac agcttggaga tg                                              22

<210> SEQ ID NO 38
<211> LENGTH: 34
<212> TYPE: DNA
<213> ORGANISM: Homo sapiens
<220> FEATURE:
<221> NAME/KEY: misc_feature
<223> OTHER INFORMATION: Section of CXCR4 gene containing DNA sequence
      of primary binding site

<400> SEQUENCE: 38
gtgaccgctt ctaccccaat gacttgtggg tggt                                 34

<210> SEQ ID NO 39
<211> LENGTH: 34
<212> TYPE: DNA
<213> ORGANISM: Homo sapiens
<220> FEATURE:
<221> NAME/KEY: misc_feature
<223> OTHER INFORMATION: Section of CXCR4 gene containing DNA sequence
      of primary binding site

<400> SEQUENCE: 39
accacccaca agtcattggg gtagaagcgg tcac                                 34

<210> SEQ ID NO 40
<211> LENGTH: 33

```
<212> TYPE: DNA
<213> ORGANISM: Homo sapiens
<220> FEATURE:
<221> NAME/KEY: misc_feature
<223> OTHER INFORMATION: Section of CXCR4 gene containing DNA sequence
      of primary binding site

<400> SEQUENCE: 40
cacgcttccc ttctgggcag ttgatgccgt ggc                                   33

<210> SEQ ID NO 41
<211> LENGTH: 33
<212> TYPE: DNA
<213> ORGANISM: Homo sapiens
<220> FEATURE:
<221> NAME/KEY: misc_feature
<223> OTHER INFORMATION: Section of CXCR4 gene containing DNA sequence
      of primary binding site

<400> SEQUENCE: 41
gccacggcat caactgccca gaagggaagc gtg                                   33

<210> SEQ ID NO 42
<211> LENGTH: 36
<212> TYPE: DNA
<213> ORGANISM: Homo sapiens
<220> FEATURE:
<221> NAME/KEY: misc_feature
<223> OTHER INFORMATION: Section of CXCR4 gene containing DNA sequence
      of primary binding site

<400> SEQUENCE: 42
ccatcgtcca cgccaccaac agtcagaggc caagga                                36

<210> SEQ ID NO 43
<211> LENGTH: 36
<212> TYPE: DNA
<213> ORGANISM: Homo sapiens
<220> FEATURE:
<221> NAME/KEY: misc_feature
<223> OTHER INFORMATION: Section of CXCR4 gene containing DNA sequence
      of primary binding site

<400> SEQUENCE: 43
tccttggcct ctgactgttg gtggcgtgga cgatgg                                36

<210> SEQ ID NO 44
<211> LENGTH: 29
<212> TYPE: DNA
<213> ORGANISM: Artificial Sequence
<220> FEATURE:
<223> OTHER INFORMATION: Synthetic DNA: A66seq1

<400> SEQUENCE: 44
gtgaccgctt ctacccctct gtgggtggt                                        29

<210> SEQ ID NO 45
<211> LENGTH: 26
<212> TYPE: DNA
<213> ORGANISM: Artificial Sequence
<220> FEATURE:
<223> OTHER INFORMATION: Synthetic DNA: A66seq2

<400> SEQUENCE: 45
gtgaccgctt ctgacttgtg ggtggt                                           26

<210> SEQ ID NO 46
```

```
<211> LENGTH: 40
<212> TYPE: DNA
<213> ORGANISM: Homo sapiens
<220> FEATURE:
<221> NAME/KEY: misc_feature
<223> OTHER INFORMATION: Section of CXCR4 gene containing DNA sequence
      of primary binding site

<400> SEQUENCE: 46
atatctgtga ccgcttctac cccaatgact tgtgggtggt                              40

<210> SEQ ID NO 47
<211> LENGTH: 28
<212> TYPE: DNA
<213> ORGANISM: Artificial Sequence
<220> FEATURE:
<223> OTHER INFORMATION: Synthetic DNA: B4seq1

<400> SEQUENCE: 47
atatctgtga ccgcttctac ccggtggt                                          28

<210> SEQ ID NO 48
<211> LENGTH: 21
<212> TYPE: DNA
<213> ORGANISM: Artificial Sequence
<220> FEATURE:
<223> OTHER INFORMATION: Synthetic DNA: B4seq2

<400> SEQUENCE: 48
atatcttgac ttgtgggtgg t                                                 21

<210> SEQ ID NO 49
<211> LENGTH: 73
<212> TYPE: DNA
<213> ORGANISM: Homo sapiens
<220> FEATURE:
<221> NAME/KEY: misc_feature
<223> OTHER INFORMATION: Section of CXCR4 gene containing DNA sequence
      of primary binding site

<400> SEQUENCE: 49
aggcagatga cagatatatc tgtgaccgct tctaccccaa tgacttgtgg gtggttgtgt       60
tccagtttca gca                                                          73

<210> SEQ ID NO 50
<211> LENGTH: 60
<212> TYPE: DNA
<213> ORGANISM: Artificial Sequence
<220> FEATURE:
<223> OTHER INFORMATION: Synthetic DNA: B13seq1

<400> SEQUENCE: 50
aggcagatga cagatatatc tgtgaccgct tctacctgtg ggtggttgtg ttccagtttc       60

<210> SEQ ID NO 51
<211> LENGTH: 40
<212> TYPE: DNA
<213> ORGANISM: Artificial Sequence
<220> FEATURE:
<223> OTHER INFORMATION: Synthetic DNA: B13seq2

<400> SEQUENCE: 51
aggcagatga cagatatatc tgtggttgtg ttccagtttc                             40

<210> SEQ ID NO 52
<211> LENGTH: 15
```

-continued

```
<212> TYPE: DNA
<213> ORGANISM: Artificial Sequence
<220> FEATURE:
<223> OTHER INFORMATION: Synthetic DNA: B13seq3

<400> SEQUENCE: 52
aggcagtcca gtttc                                                    15
```

US 8,871,905 B2

MODIFICATION OF CXCR4 USING ENGINEERED ZINC FINGER PROTEINS

CROSS-REFERENCE TO RELATED APPLICATIONS

This application claims the benefit of U.S. Provisional Application No. 61/210,636 filed Mar. 20, 2009 and U.S. Provisional Application No. 61/273,861 filed Aug. 10, 2009, the disclosures of which are hereby incorporated by reference in their entireties herein.

STATEMENT OF RIGHTS TO INVENTIONS MADE UNDER FEDERALLY SPONSORED RESEARCH

Not applicable.

TECHNICAL FIELD

The present disclosure is in the field of genome modification of human cells, including lymphocytes and stem cells.

BACKGROUND

Various methods and compositions for targeted cleavage of genomic DNA have been described. Such targeted cleavage events can be used, for example, to induce targeted mutagenesis, induce targeted deletions of cellular DNA sequences, and facilitate targeted recombination at a predetermined chromosomal locus. See, for example, United States Patent Publications 20030232410; 20050208489; 20050026157; 20050064474; 20060188987; 2008015996, and International Publication WO 2007/014275, the disclosures of which are incorporated by reference in their entireties for all purposes. See, also, Santiago et al. (2008) *Proc Nat'l Aced Sic USA* 105:5809-5814; Perez et al. (2008) *Nat Biotechnol* 26:808-816 (2008).

For HIV, the most important co-receptors in vivo are CCR5, a 7-transmembrane chemokine receptor, and CXCR4 (a CXC chemokine receptor). See, e.g., Feng et al. (1996) *Science* 272:872-877; Deng et al. (1996) *Nature* 381:661-666; Schuitemaker et al. (1999) *J. Virol.* 73:5373-5380. HIV type 1 (HIV-1) strains that use only CCR5 (R5 viruses), predominate during the early stages of infection and are critical for transmission (Schuitemaker et al. (1992) *J. Virol.* 66:1354-1360; van't Wout et al. (1994) *J. Clin. Invest.* 94:2060-2067). Although R5 viruses generally persist in late stage disease, viruses that can use CXCR4, either exclusively (X4 viruses) or in addition to CCR5 (R5X4 viruses), emerge in approximately 50% of subtype B-infected individuals (Connor et al. (1997) *J. Exp. Med.* 185:621-628; Karlsson et al. (1994) *J. Clin. Microbiol.* 32:364-370). This co-receptor switch is associated with a more rapid decline in peripheral blood CD4+ T cells and a faster progression to AIDS (Richman, D. et al. (1994) *J. Infect. Dis.* 169:968-974).

Thus, there remains a need for compositions that knock-out CXCR4 for treatment and prevention of CXCR4-tropic HIV infection.

SUMMARY

Disclosed herein are compositions and methods for partial or complete inactivation of CXCR4. In particular described herein are nucleases (e.g., zinc finger nucleases) that can be used to inactivate CXCR4. The CXCR4 nucleases described herein are useful in generating cell lines (CXCR4-lines) which can be used to study the function(s) of CXCR4 under physiological or pathological conditions. Furthermore, the nucleases described herein can also be used ex vivo or in vivo as therapeutic reagents for treating certain diseases including HIV-1 infections.

In one aspect, provided herein are zinc finger nucleases (ZFNs) that have target sites in the human CXCR4 gene. In some embodiments, cleavage within the CXCR4 gene with these nucleases results in permanent disruption (e.g., mutation) of the CXCR4 gene. In certain embodiments, the zinc finger domain(s) is(are) engineered to bind to a target site within the ECL-2 domain of a CXCR4 gene. The zinc finger proteins may include 1, 2, 3, 4, 5, 6 or more zinc fingers, each zinc finger having a recognition helix that binds to a target subsite in the target gene. In certain embodiments, the zinc finger proteins comprise 4 or 5 fingers (designated F1, F2, F3, F4 and F5 and ordered F1 to F4 or F5 from N-terminus to C-terminus) and the fingers comprise the amino acid sequence of the recognition regions shown in Table 1.

Any of the proteins described herein may further comprise a cleavage domain and/or a cleavage half-domain (e.g., a wild-type or engineered FokI cleavage half-domain). Thus, in any of the ZFNs described herein, the nuclease domain may comprise a wild-type nuclease domain or nuclease half-domain (e.g., a FokI cleavage half domain). In other embodiments, the ZFNs comprise engineered nuclease domains or half-domains, for example engineered FokI cleavage half domains that form obligate heterodimers. See, e.g., U.S. Patent Publication No. 20080131962.

In another aspect, the disclosure provides a polynucleotide encoding any of the proteins described herein. Any of the polynucleotides described herein may also comprise sequences (donor or patch sequences) for targeted insertion into the CXCR4 gene.

In yet another aspect, a gene delivery vector comprising any of the polynucleotides described herein is provided. In certain embodiments, the vector is an adenovirus vector (e.g., an Ad5/F35 vector). Thus, also provided herein are adenovirus (Ad) vectors comprising a sequence encoding at least one zinc finger nuclease (ZFN) and/or a donor sequence for targeted integration into a target gene. In certain embodiments, the Ad vector is a chimeric Ad vector, for example an Ad5/F35 vector. In additional embodiments, the target gene is the human CXCR4 gene. The vectors described herein may also comprise donor sequences. In certain embodiments, a single vector comprises sequences encoding one or more ZFNs and the donor sequence(s). In other embodiments, the donor sequence(s) are contained in a first vector and the ZFN-encoding sequences are present in a second vector.

In yet another aspect, the disclosure provides an isolated cell comprising any of the proteins, polynucleotides and/or vectors described herein. In certain embodiments, the cell is selected from the group consisting of a hematopoietic stem cell, a T-cell (e.g., CD4+ T-cell), a macrophage, a dendritic cell and an antigen-presenting cell. Cells include, for example, peripheral Blood Mononuclear Cells (PBMCs), macrophages, mesenchymal stem cells, human embryonic stem cells (hES cells), hematopoietic stem cells (e.g., CD34+ cells), T-cells (e.g., CD4+ cells), dendritic cells or antigen-presenting cells; or a cell line such as K562 (chronic myelogenous leukemia), HEK293 (embryonic kidney), PM-1 (CD4+ T-cell), Sup-T1 (lymphoblastic leukemia), THP-1 (monocytic leukemia) or GHOST (osteosarcoma). In another aspect, cell lines in which CXCR4 has been inactivated are provided.

In another aspect, described herein are methods of inactivating a CXCR4 gene in a cell by introducing one or more proteins, polynucleotides and/or vectors into the cell as described herein. In any of the methods described herein the ZFNs may induce targeted mutagenesis, targeted deletions of cellular DNA sequences, and/or facilitate targeted recombination at a predetermined chromosomal locus. Thus, in certain embodiments, the ZFNs delete one or more nucleotides of the target gene. In some embodiments the CXCR4 gene is inactivated after ZFN cleavage followed by non-homologous end joining. In other embodiments, a genomic sequence in the target gene is replaced, for example using a ZFN (or vector encoding said ZFN) as described herein and a "donor" sequence that is inserted into the gene following targeted cleavage with the ZFN. The donor sequence may be present in the ZFN vector, present in a separate vector (e.g., Ad vector) or, alternatively, may be introduced into the cell using a different nucleic acid delivery mechanism.

In another aspect, methods of using the zinc finger proteins and fusions thereof for mutating the CXCR4 gene and/or inactivating CXCR4 function in a cell or cell line are provided. Thus, a method for inactivating a CXCR4 gene in a human cell is provided, the method comprising administering to the cell any of the proteins or polynucleotides described herein.

In yet another aspect, the disclosure provides a method for treating or preventing HIV infection in a subject, the method comprising: (a) introducing, into a cell, a first nucleic acid encoding a first polypeptide, wherein the first polypeptide comprises: (i) a zinc finger DNA-binding domain that is engineered to bind to a first target site in a CXCR4 gene; and (ii) a cleavage domain; under conditions such that the polypeptide is expressed in the cell, whereby the polypeptide binds to the target site and cleaves the CXCR4 gene; and (b) introducing the cell into the subject. In certain embodiments, the cell is selected from the group consisting of a hematopoietic stem cell, a T-cell, a macrophage, a dendritic cell or an antigen-presenting cell. The nucleic acid may comprise any of the polynucleotides described herein. In any of the methods, the first nucleic acid may further encode a second polypeptide, wherein the second polypeptide comprises: (i) a zinc finger DNA-binding domain that is engineered to bind to a second target site in the CXCR4 gene; and (ii) a cleavage domain; such that the second polypeptide is expressed in the cell, whereby the first and second polypeptides bind to their respective target sites and cleave the CXCR4 gene. Similarly, any of these methods may further comprise the step of introducing into the cell a second nucleic acid, wherein the second nucleic acid contains two regions of homology to the CXCR4 gene, flanking a sequence that is non-homologous to a CXCR4 gene. These methods may be used to make changes in the gene sequence encoding CXCR4, i.e., by including the desired changes into the second nucleic acid that is integrated into the CXCR4 gene. Using these methods, both large and small modifications in the gene sequence, including modifications (alteration or deletion) to 1 nucleotide. In some aspects, the invention provides methods and compositions where the CXCR4-specific ZFNs are used in combination with CCR5-specific ZFNS (see, e.g., US Patent Application 20080159996). The CXCR4- and CCR5-specific ZFNs may be supplied together on a single delivery vehicle or may be supplied separately. Similarly, the CXCR4- and CCR5-specific ZFNs may be supplied concurrently of sequentially.

In any of the methods and compositions described herein, the cell can be, for example, a hematopoietic stem cell (e.g., a $CD34^+$ cell), a T-cell (e.g., a $CD4^+$ cell), a macrophage, a dendritic cell or an antigen-presenting cell; or a cell line such as K562 (chronic myelogenous leukemia), HEK293 (embryonic kidney), PM-1 ($CD4^+$ T-cell), Sup-T1 (lymphoblastic leukemia), THP-1 (monocytic leukemia) or GHOST (osteosarcoma).

Furthermore, any of the methods described herein can be practiced in vitro; in vivo and/or ex vivo. In certain embodiments, the methods are practiced ex vivo, for example to modify PBMCs, e.g., T-cells, to make them resistant to HIV infection via disruption of CXCR4. In certain embodiments, the methods are practiced in vivo, for example by administering the CXCR4-specific ZFNs to a patients afflicted by HIV. In other aspects, the methods are practices in vivo by administering both CXCR4- and CCR5-specific ZFNs to patients afflicted by HIV.

BRIEF DESCRIPTION OF THE DRAWINGS

FIG. 1, panels A to C, depict targeting the CXCR4 gene with designed ZFNs. FIGS. 1A to C show ZFN binding sites and recognition helix sequences. Sections of CXCR4 gene containing DNA sequence of the primary binding site (underlined) for each ZFN are shown. The amino acid sequence of the recognition helix of each ZFN from position −1 to +6 is listed below its target DNA triplet.

FIG. 2, panels A and D, depict modification of CXCR4 by ZFNs. FIGS. 2B-2D depict genotype sequence analysis of the indicated single cell-derived clones. Sections of CXCR4 gene containing DNA sequence of the primary binding site (underlined) for 12273/12270 ZFNs are used as reference sequences for alignment. A dash ("-") indicates a deletion; bolded letters indicate an insertion.

FIGS. 3A and 3B show that the R5/X4 tropic viruses HIV-1 R3A (FIG. 3A) and SF2 (FIG. 3B) are able to productively infect SupT1 cells but not the SupT1 clones B13 or A66. FIG. 3C shows the same selectivity for the strictly X4 tropic HIV-1 BK132 virus.

FIG. 6A shows the growth curve of mock HIV-1 infected cells. FIGS. 6B, 6C and 6D show the growth curve of BK132 cells, HxB cells and R3A cells, respectively, at the indicated times post-transduction. Cells treated with CXCR4-specific ZFNs were more resistant to the lethal effect of CXCR4-tropic HIV strains.

FIG. 7A shows the growth curve of mock HIV-1 infected cells. FIGS. 7B, 7C and 7D show the growth curve of BK132 cells, HxB cells and R3A cells, respectively, at the indicated times post-transduction. Cells treated with CXCR4-specific ZFNs were more resistant to the lethal effect of CXCR4-tropic or R5/X4-tropic HIV strains.

FIG. 10A depicts the engraftment of the T cells in the mice and demonstrates that both the CXCR4-specific ZFN treated cells (X4ZFN) and the CCR5-specific ZFN treated cells (R5ZFN) engrafted equally well. FIG. 10B depicts the amount of CXCR4 expression on the surface of the engrafted cells that had been treated with either CXCR4-specific ZFNs or CCR5-specific ZFNs prior to engraftment. As expected, the cells treated with the CXCR4-specific ZFNs (X4ZFN) displayed a lower level of CXCR4 expression than those cells that had been treated with the CCR5-specific ZFNs (R5ZFN).

DETAILED DESCRIPTION

Figure 1D:
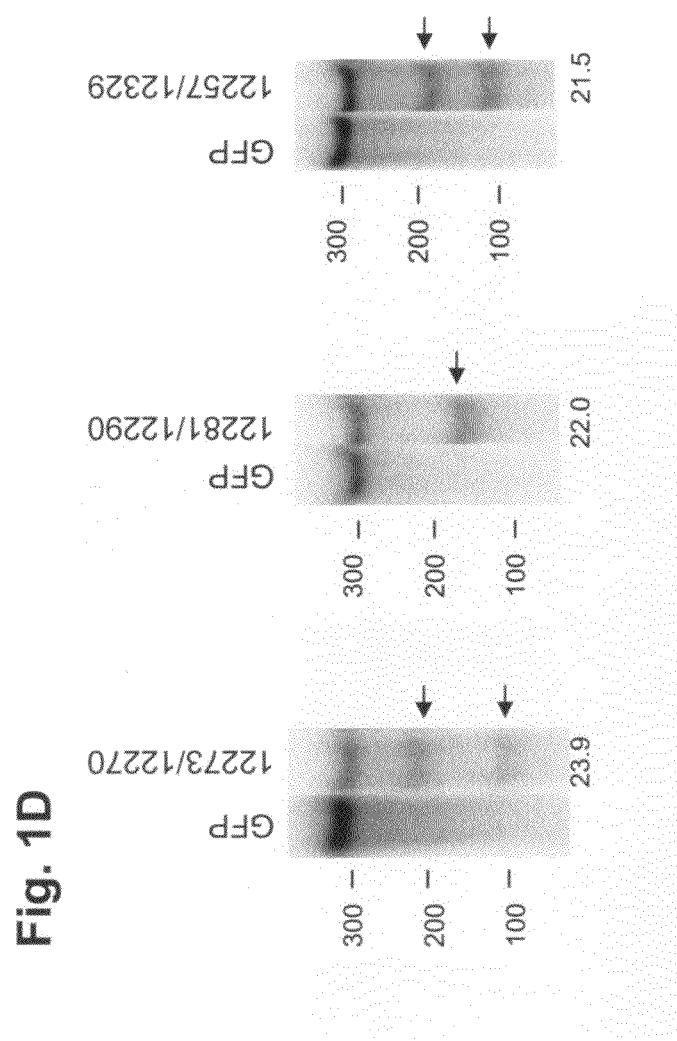
FIG. 1D shows the percentage of disrupted CXCR4 alleles modified via non-homologous end joining (NHEJ) after treatment with designed ZFNs as assayed by Surveyor™ nuclease assay. Positions of 100 by DNA ladder (Invitrogen) are indicated on the left of each gel. Cleaved CXCR4 PCR products are indicated by arrows. Numbers at the bottom of each lane indicate calculated frequency of modification by NHEJ (%).

Disclosed herein are zinc finger nucleases (ZFNs) targeting a CXCR4 gene (CXCR4-ZFNs). These ZFNs efficiently generate a double strand break (DSB), for example at a predetermined site in a CXCR4 coding region. The site can be, for example, in the ECL-2 domain of a CXCR4 gene (e.g., human gene). ZFN-mediated introduction of a site-specific double strand break (DSB) in CXCR4 resulted in the specific and permanent disruption of the targeted CXCR4 gene in human lymphoid cell lines.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains (e.g., the recognition helix region) can be "engineered" to bind to a predetermined nucleotide sequence. The engineered region of the zinc finger is typically the recognition helix, particularly the portion of the alpha-helical region numbered −1 to +6. Backbone sequences for an engineered recognition helix are known in the art. See, e.g., Miller et al. (2007) *Nat Biotechnol* 25, 778-785. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc finger protein is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; WO 95/19431; WO 96/06166; WO 98/53057; WO 98/54311; WO 00/27878; WO 01/60970 WO 01/88197 and WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present disclosure is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects sequence identity. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the internet. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *Nucleic Acid Hybridization: A Practical Approach*, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and – cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 20050064474 and 20060188987 and U.S. Provisional Application No. 60/808,486 (filed May 25, 2006), incorporated herein by reference in their entireties.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression.

"Eukaryotic" cells include, but are not limited to, fungal cells (such as yeast), plant cells, animal cells, mammalian cells and human cells (e.g., T-cells).

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) Nature 340:245-246; U.S. Pat. No. 5,585,245 and PCT WO 98/44350.

Zinc Finger Nucleases and Zinc Finger Transcription Factors

Described herein are zinc finger nucleases (ZFNs) and zinc finger transcription factors (ZF-TFs) that can be used for inactivation and/or modulation of expression of a CXCR4 gene. ZFNs comprise a zinc finger protein (ZFP) and a nuclease (cleavage) domain. ZF-TFs comprise a zinc finger protein (ZFP) and a functional transcriptional regulatory domain.

A. Zinc Finger Proteins

Zinc finger binding domains can be engineered to bind to a sequence of choice. See, for example, Beerli et al. (2002) Nature Biotechnol. 20:135-141; Pabo et al. (2001) Ann. Rev. Biochem. 70:313-340; Isalan et al. (2001) Nature Biotechnol. 19:656-660; Segal et al. (2001) Curr. Opin. Biotechnol. 12:632-637; Choo et al. (2000) Curr. Opin. Struct. Biol. 10:411-416. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

Enhancement of binding specificity for zinc finger binding domains has been described, for example, in co-owned WO 02/077227.

Selection of target sites; ZFPs and methods for design and construction of fusion proteins (and polynucleotides encoding same) are known to those of skill in the art and described in detail in related to U.S. Publication Nos. 20030232410; 20050208489; 2005064474; 20050026157; 20060188987; International Publication WO 07/014,275; U.S. patent application Ser. Nos. 10/587,723 (filed Jul. 27, 2006); 11/493,423 (filed Jul. 26, 2006), the disclosures of which are incorporated by reference in their entireties for all purposes.

The zinc finger proteins described herein bind to a target site in a CXCR4 gene. Table 1 (see Example 1) describes a number of zinc finger binding domains that have been engineered to bind to nucleotide sequences in the human CXCR4 gene. The DNA target sequence for each domain is shown in the first column (DNA target sites indicated in uppercase letters; non-contacted nucleotides indicated in lowercase), and the second through fifth columns show the amino acid sequence of the recognition region (amino acids −1 through +6, with respect to the start of the helix) of each of the zinc fingers (F1 through F4 or F5) in the protein. Also provided in the first column is an identification number for each protein.

As described below, in certain embodiments, a four- or five-finger binding domain as shown in Table 1 is fused to functional domain, for example an activation domain or a cleavage half-domain, such as, for example, the cleavage domain of a Type IIs restriction endonuclease such as FokI. A pair of such zinc finger/nuclease half-domain fusions are used for targeted cleavage, as disclosed, for example, in U.S. Patent Publication No. 20050064474 (application Ser. No. 10/912,932).

For targeted cleavage using a ZFN, the near edges of the binding sites can separated by 5 or more nucleotide pairs, and each of the fusion proteins can bind to an opposite strand of the DNA target.

The CXCR4-ZFPs described herein can be targeted to any sequence in any CXCR4 genomic sequence.

B. Cleavage Domains

In certain embodiments, the ZFPs are ZFNs comprising a nuclease (cleavage domain, cleavage half-domain). The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014,275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987; 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in certain embodiments, the mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". In one embodiment, the mutation at 490 replaces Glu (E) with Lys (K); the mutation at 538 replaces Ile (I) with Lys (K); the mutation at position 537 replaces His (H) with Lys (K) or Arg (R); the mutation at 486 replaced Gln (Q) with Glu (E); the mutation at position 499 replaces Ile (I) with Leucine (L); and the mutation at 496 replaces Asn (N) with Asp (D) or Glu (E). Specifically, the engineered cleavage half-domains described herein were prepared by mutating positions 490 (E→K), 538 (I→K), and 537 (H→K or H→R) in one cleavage half-domain to produce engineered cleavage half-domains designated "E490K:I538K:H537K" (KKK) or"E490K:I538K:H537R" (KKR) and by mutating positions 486 (Q→E), 499 (I→L) and 496 (N→D or N→E) in another cleavage half-domain to produce engineered cleavage half-domains designated "Q486E:I499L:N496E" (ELE) or "Q486E:I499L:N496D" (ELD). The engineered cleavage half-domains described herein are obligate heterodimer mutants in which aberrant cleavage is minimized or abolished. See, e.g., Example 1 of U.S. Patent Publication No. 2008/0131962, the disclosure of which is incorporated by reference in its entirety for all purposes. See also U.S. Provisional Patent Application 61/337,769. See, also, Szczepek et al. (2007) *Nat Biotechnol* 25:786-793.

Engineered cleavage half-domains described herein can be prepared using any suitable method, for example, by site-directed mutagenesis of wild-type cleavage half-domains (Fok I) as described in U.S. Patent Publication Nos. 20050064474 and 20080131962.

In other embodiments, the cleavage domain comprises a naturally occurring or engineered meganuclease cleavage domain. For example, engineering of homing endonucleases with tailored DNA-binding specificities has been described, see Chames et al. (2005) *Nucleic Acids Res* 33(20):e178; Arnould et al. (2006) *J. Mol. Biol.* 355:443-458 and Grizot et al (2009) *Nucleic Acids Res* July 7 e publication. In addition, engineering of ZFPs has also been described. See, e.g., U.S. Pat. Nos. 6,534,261; 6,607,882; 6,824,978; 6,979,539; 6,933,113; 7,163,824; and 7,013,219.

Naturally-occurring meganucleases recognize 15-40 base-pair cleavage sites and are commonly grouped into four families: the LAGLIDADG family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

DNA-binding domains from naturally-occurring meganucleases, primarily the LAGLIDADG family, have been used to promote site-specific genome modification in plants, yeast, *Drosophila*, mammalian cells and mice, but this approach has been limited to the modification of either homologous genes that conserve the meganuclease recognition sequence (Monet et al. (1999), *Biochem. Biophysics. Res. Common.* 255: 88-93) or to pre-engineered genomes into which a recognition sequence has been introduced (Route et al. (1994), *Mol. Cell. Biol.* 14: 8096-106; Chilton et al. (2003), *Plant Physiology.* 133: 956-65; Puchta et al. (1996), *Proc. Natl. Acad. Sci. USA* 93: 5055-60; Rong et al. (2002), *Genes Dev.* 16: 1568-81; Gouble et al. (2006), *J. Gene Med.* 8(5):616-622). Accordingly, attempts have been made to engineer meganucleases to exhibit novel binding specificity at medically or biotechnologically relevant sites (Porteus et al. (2005), *Nat. Biotechnol.* 23: 967-73; Sussman et al. (2004), *J. Mol. Biol.* 342: 31-41; Epinat et al. (2003), *Nucleic Acids Res.* 31: 2952-62; Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication Nos. 20070117128; 20060206949; 20060153826; 20060078552; and 20040002092). In addition, naturally-occurring or engineered DNA-binding domains from meganucleases have also been operably linked with a cleavage domain from a heterologous nuclease (e.g., FokI).

C. Additional Zinc Finger Fusion Proteins

In other embodiments, fusion proteins comprising DNA-binding proteins (e.g., ZFPs) as described herein and a heterologous regulatory (functional) domain (or functional fragment thereof) are also provided. Common domains include, e.g., transcription factor domains (activators, repressors, co-activators, co-repressors), silencers, oncogenes (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g. kinases, acetylases and deacetylases); and DNA modifying enzymes (e.g., methyltransferases, topoisomerases, helicases, ligases, kinases, phosphatases, polymerases, endonucleases) and their associated factors and modifiers. U.S. Patent Application Publication Nos. 20050064474; 20060188987 and 2007/0218528 for details regarding fusions of DNA-binding domains and nuclease cleavage domains, incorporated by reference in their entireties herein.

Suitable domains for achieving activation include the HSV VP16 activation domain (see, e.g., Hagmann et al., *J. Virol.* 71, 5952-5962 (1997)) nuclear hormone receptors (see, e.g., Torchia et al., *Curr. Opin. Cell. Biol.* 10:373-383 (1998)); the p65 subunit of nuclear factor kappa B (Bitko & Barik, *J. Virol.* 72:5610-5618 (1998) and Doyle & Hunt, *Neuroreport* 8:2937-2942 (1997)); Liu et al., *Cancer Gene Ther.* 5:3-28 (1998)), or artificial chimeric functional domains such as VP64 (Beerli et al., (1998) *Proc. Natl. Acad. Sci. USA* 95:14623-33), and degron (Molinari et al., (1999) *EMBO J.* 18, 6439-6447). Additional exemplary activation domains include, Oct 1, Oct-2A, Sp1, AP-2, and CTF1 (Seipel et al., *EMBO J.* 11, 4961-4968 (1992) as well as p300, CBP, PCAF, SRC1 PvALF, AtHD2A and ERF-2. See, for example, Robyr et al. (2000) *Mol. Endocrinol.* 14:329-347; Collingwood et al. (1999) *Mol. Endocrinol.* 23:255-275; Leo et al. (2000) *Gene* 245:1-11; Manteuffel-Cymborowska (1999) *Acta Biochim. Pol.* 46:77-89; McKenna et al. (1999) *J. Steroid Biochem. Mol. Biol.* 69:3-12; Malik et al. (2000) *Trends Biochem. Sci.* 25:277-283; and Lemon et al. (1999) *Curr. Opin. Genet. Dev.* 9:499-504. Additional exemplary activation domains include, but are not limited to, OsGAI, HALF-1, C1, AP1, ARF-5, -6, -7, and -8, CPRF1, CPRF4, MYC-RP/GP, and TRAB1. See, for example, Ogawa et al. (2000) *Gene* 245:21-29; Okanami et al. (1996) *Genes Cells* 1:87-99; Goff et al. (1991) *Genes Dev.* 5:298-309; Cho et al. (1999) *Plant Mol. Biol.* 40:419-429; Ulmason et al. (1999) *Proc. Natl. Acad. Sci. USA* 96:5844-5849; Sprenger-Haussels et al. (2000) *Plant J.* 22:1-8; Gong et al. (1999) *Plant Mol. Biol.* 41:33-44; and Hobo et al. (1999) *Proc. Natl. Acad. Sci. USA* 96:15,348-15,353.

It will be clear to those of skill in the art that, in the formation of a fusion protein (or a nucleic acid encoding same) between a DNA-binding domain (ZFP) and a functional domain, either an activation domain or a molecule that interacts with an activation domain is suitable as a functional domain. Essentially any molecule capable of recruiting an activating complex and/or activating activity (such as, for example, histone acetylation) to the target gene is useful as an activating domain of a fusion protein. Insulator domains, localization domains, and chromatin remodeling proteins such as ISWI-containing domains and/or methyl binding domain proteins suitable for use as functional domains in fusion molecules are described, for example, in co-owned U.S. Patent Applications 2002/0115215 and 2003/0082552 and in co-owned WO 02/44376.

Exemplary repression domains include, but are not limited to, KRAB A/B, KOX, TGF-beta-inducible early gene (TIEG), v-erbA, SID, MBD2, MBD3, members of the DNMT family (e.g., DNMT1, DNMT3A, DNMT3B), Rb, and MeCP2. See, for example, Bird et al. (1999) *Cell* 99:451-454; Tyler et al. (1999) *Cell* 99:443-446; Knoepfler et al. (1999) *Cell* 99:447-450; and Robertson et al. (2000) *Nature Genet.* 25:338-342. Additional exemplary repression domains include, but are not limited to, ROM2 and AtHD2A. See, for example, Chem et al. (1996) *Plant Cell* 8:305-321; and Wu et al. (2000) *Plant J.* 22:19-27.

Fusion molecules are constructed by methods of cloning and biochemical conjugation that are well known to those of skill in the art. Fusion molecules comprise a DNA-binding domain and a functional domain (e.g., a transcriptional activation or repression domain). Fusion molecules also optionally comprise nuclear localization signals (such as, for example, that from the SV40 medium T-antigen) and epitope tags (such as, for example, FLAG and hemagglutinin). Fusion proteins (and nucleic acids encoding them) are designed such that the translational reading frame is preserved among the components of the fusion.

Fusions between a polypeptide component of a functional domain (or a functional fragment thereof) on the one hand, and a non-protein DNA-binding domain (e.g., antibiotic, intercalator, minor groove binder, nucleic acid) on the other, are constructed by methods of biochemical conjugation known to those of skill in the art. See, for example, the Pierce Chemical Company (Rockford, Ill.) Catalogue. Methods and compositions for making fusions between a minor groove binder and a polypeptide have been described. Mapp et al. (2000) *Proc. Natl. Acad. Sci. USA* 97:3930-3935.

In certain embodiments, the target site bound by the zinc finger protein is present in an accessible region of cellular chromatin. Accessible regions can be determined as described, for example, in co-owned International Publication WO 01/83732. If the target site is not present in an accessible region of cellular chromatin, one or more accessible regions can be generated as described in co-owned WO 01/83793. In additional embodiments, the DNA-binding domain of a fusion molecule is capable of binding to cellular chromatin regardless of whether its target site is in an accessible region or not. For example, such DNA-binding domains are capable of binding to linker DNA and/or nucleosomal DNA. Examples of this type of "pioneer" DNA binding domain are found in certain steroid receptor and in hepatocyte nuclear factor 3 (HNF3). Cordingley et al. (1987) *Cell* 48:261-270; Pina et al. (1990) *Cell* 60:719-731; and Cirillo et al. (1998) *EMBO J.* 17:244-254.

The fusion molecule may be formulated with a pharmaceutically acceptable carrier, as is known to those of skill in the art. See, for example, Remington's Pharmaceutical Sciences, 17th ed.; 1985; and co-owned WO 00/42219.

The functional component/domain of a fusion molecule can be selected from any of a variety of different components capable of influencing transcription of a gene once the fusion molecule binds to a target sequence via its DNA binding domain. Hence, the functional component can include, but is not limited to, various transcription factor domains, such as activators, repressors, co-activators, co-repressors, and silencers.

Additional exemplary functional domains are disclosed, for example, in co-owned U.S. Pat. No. 6,534,261 and US Patent Application Publication No. 2002/0160940.

Functional domains that are regulated by exogenous small molecules or ligands may also be selected. For example, RheoSwitch® technology may be employed wherein a functional domain only assumes its active conformation in the presence of the external RheoChem™ ligand (see for example US 20090136465). Thus, the ZFP may be operably linked to the regulatable functional domain wherein the resultant activity of the ZF-TF is controlled by the external ligand.

D. Additional Methods for Targeted Modification in CXCR4

Any nuclease can be used in the methods disclosed herein. For example, naturally-occurring homing endonucleases and meganucleases have very long recognition sequences, some of which are likely to be present, on a statistical basis, once in a human-sized genome. Exemplary homing endonucleases include I-SceI, I-CeuI, PI-PspI, PI-Sce, I-SceIV, I-SceIII, I-CreI, I-TevI, I-TevII and I-TevIII. Their recognition sequences are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

It has also been reported that the specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441: 656-659; Paques et al. (2007) *Current Gene Therapy* 7:49-66.

In some embodiments, the DNA binding domain is an engineered domain from a TAL effector derived from the plant pathogen *Xanthomonas* (see Boch et al, *Science*. 2009 Dec. 11; 326(5959):1509-12. and Moscou and Bogdanove, *Science*. 2009 Dec. 11; 326(5959):1501.

Thus, any naturally occurring or engineered nuclease having a unique target site can be used instead of, or in addition to, a zinc finger nuclease, for targeted integration of sequences such as lineage-specific reporters into stem cells. In addition, domains from these naturally occurring or engineered nucleases can also be isolated and used in various combinations. For example, the DNA-binding domain from a naturally occurring or engineered homing endonucleases or meganuclease can be fused to a heterologous cleavage domain or half domain (e.g., from another homing endonuclease, meganuclease or TypeIIS endonuclease). These fusion proteins can also be used in combination with zinc finger nucleases described above.

Delivery

The ZFNs described herein may be delivered to a target cell containing a CXCR4 gene by any suitable means. Methods of delivering proteins comprising zinc fingers are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

ZFNs as described herein may also be delivered using vectors containing sequences encoding one or more ZFNs. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties.

In certain embodiments, the vector is an adenovirus vector. Non-limiting examples of Ad vectors that can be used in the present application include recombinant (such as E1-deleted), conditionally replication competent (such as oncolytic) and/or replication competent Ad vectors derived from human or non-human serotypes (e.g., Ad5, Ad11, Ad35, or porcine adenovirus-3); and/or chimeric Ad vectors (such as Ad5/F35) or tropism-altered Ad vectors with engineered fiber (e.g., knob or shaft) proteins (such as peptide insertions within the HI loop of the knob protein). Also useful are "gutless" Ad vectors, e.g., an Ad vector in which all adenovirus genes have been removed, to reduce immunogenicity and to increase the size of the DNA payload. This allows, for example, simultaneous delivery of sequences encoding ZFNs and a donor sequence. Such gutless vectors are especially useful when the donor sequences include large transgenes to be integrated via targeted integration.

Replication-deficient recombinant adenoviral vectors (Ad) can be produced at high titer, and they readily infect a number of different cell types. Most adenovirus vectors are engineered such that a transgene replaces the Ad E1a, E1b, and/or E3 genes; subsequently the replication defective vector is propagated in cells that provide one or more of the deleted gene functions in trans. For example, human 293 cells supply E1 function. Ad vectors can transduce multiple types of tissues in vivo, including non-dividing, differentiated cells such as those found in liver, kidney and muscle.

Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-1089 (1998)).

Additional examples of the use of adenovirus vectors for gene transfer in clinical trials include Rosenecker et al., *Infection* 24:1 5-10 (1996); Welsh et al., *Hum. Gene Ther.* 2:205-18 (1995); Alvarez et al., *Hum. Gene Ther.* 5:597-613 (1997); Topf et al., *Gene Ther.* 5:507-513 (1998).

In certain embodiments, the Ad vector is a chimeric adenovirus vector, containing sequences from two or more different adenovirus genomes. For example, the Ad vector can be an Ad5/F35 vector. Ad5/F35 is created by replacing one or more of the fiber protein genes (knob, shaft, tail, penton) of Ad5 with the corresponding fiber protein gene from a B group adenovirus such as, for example, Ad35. The Ad5/F35 vector and characteristics of this vector are described, for example, in Ni et al. (2005) *Hum Gene Ther* 16:664-677; Nilsson et al. (2004) *Mol Ther* 9:377-388; Nilsson et al. (2004) *J Gene Med* 6:631-641; Schroers et al. (2004) *Exp Hematol* 32:536-546; Seshidhar et al. (2003) *Virology* 311:384-393; Shayakhmetov et al. (2000) *J Virol* 74:2567-2583; and Soya et al. (2004), *Mol Ther* 9:496-509.

As noted above, ZFNs and polynucleotides encoding these ZFNs may be delivered to any target cell. Generally, for inactivating a gene, the cell is an immune cell, for example, a lymphocyte (B-cells, T-cells such as T helper ($T_H$) and T cytotoxic cells ($T_C$), null cells such as natural killer (NK) cells); a mononuclear cell (monocytes, macrophages); a granulocytic cell (granulocytes, neutrophils, eosinophils, basophils); a mast cell; and/or a dendritic cell (Langerhans cells, interstitial dendritic cells, interdigitating dendritic cells, circulating dendritic cells). Macrophages, B lymphocytes and dendritic cells are exemplary antigen-presenting cells involved in $T_H$ cell activation. In certain embodiments, the target cell is a $T_H$ cell, characterized by expression of CD4 on the surface. The target cell may also be a hematopoietic stem cell, which may give rise to any immune cell.

Applications

The disclosed methods and compositions can be used for inactivation of a CXCR4 genomic sequence. As noted above, inactivation includes partial or complete repression of CXCR4 gene expression in a cell. Inactivation of a CXCR4 gene can be achieved, for example, by a single cleavage event, by cleavage followed by non-homologous end joining, by cleavage at two sites followed by joining so as to delete the sequence between the two cleavage sites, by targeted recombination of a missense or nonsense codon into the coding region, by targeted recombination of an irrelevant sequence (i.e., a "stuffer" sequence) into the gene or its regulatory region, so as to disrupt the gene or regulatory region, or by targeting recombination of a splice acceptor sequence into an intron to cause mis-splicing of the transcript.

There are a variety of applications for ZFN-mediated inactivation (knockout or knockdown) of CXCR4. For example, the methods and compositions described herein allow for the generation and/or modification of cells lines (for therapeutic and non-therapeutic uses). The ability to knockout the CXCR4 gene, which is commonly expressed on the surface of human cells, provides the opportunity for studies of co-receptor function and HIV interactions. Moreover, future studies can now assess the consequences of CXCR4 gene knockout on primary T cell function and susceptibility to HIV-1 infection in vivo in studies in immunodeficient mice. In addition, the methods and compositions described herein can be used for the treatment and/or prevention of HIV infections in a host (e.g., by blocking expression of CXCR4, thereby preventing infection and/or spread in a host organism). Also envisioned by the invention are methods and compositions wherein the CXCR4-specific ZFNs of the invention are supplied with CCR5-specific ZFNS to simultaneously block expression of both the CXCR4 and CCR5 HIV co-receptors, for example for the treatment and/or prevention of HIV infection. These ZFN sets can be supplied either separately or may be incorporated into one delivery vehicle. The CXCR4- and CCR5-specific ZFNs may be supplied simultaneously or separately. Additionally, CXCR4 has been implicated in the oncology and the metastatic processes (see e.g. Vandercappellen et al, *Cancer Lett.* 2008 Aug. 28; 267(2):226-44). Thus, methods and compositions described herein may also be useful in the treatment of cancer and cancer-related metastasis.

CXCR4 may also have a role in retaining hematopoietic stem cells in the bone marrow, and it has been shown that blockage of CXCR4 can lead to an increase in stem cell mobilization in the periphery (See Flomenberg et al, *Acta Haematol.* 2005; 114(4):198-205). Thus, the methods of the invention (e.g., fusion proteins comprising zinc finger nucleases or inhibitory transcription factors) may be used to increase the ability of stem cells to mobilize into the blood stream and repair tissue damage in the periphery of the body. In addition, it has been shown that blockage of the CXCR4 axis can increase the speed at which progenitor and mature bone marrow cells are released following a bone marrow transplant (see Abraham et al, *Leukemia.* 2009 August; 23(8): 1378-88), and so the methods of the invention may be used to increase bone marrow transplant success by modulating expression of CXCR4 using zinc finger proteins. Also, transient upregulation of CXCR4 expression using methods of the invention (e.g. fusion proteins comprising zinc finger stimulatory transcription factors) may be used to cause homing of stem cells to the bone marrow and may improve the initial engraftment of the bone marrow transplant.

All patents, patent applications and publications mentioned herein are hereby incorporated by reference in their entireties.

Although disclosure has been provided in some detail by way of illustration and example for the purposes of clarity and understanding, it will be apparent to those of skill in the art that various changes and modifications can be practiced without departing from the spirit or scope of the disclosure. Accordingly, the foregoing disclosure and following examples should not be construed as limiting.

EXAMPLES

Example 1

Preparation of CXCR4-Targeted ZFNs

The CXCR4 gene located on human chromosome 2 has 2 exons, which encode two splice variants, isoform a and b. CXCR4 is mainly expressed on the cell surface as isoform b. As exon 1 of CXCR4 gene is only 15 by long, ZFNs targeted to exon 2 of CXCR4 were designed and incorporated into plasmids or adenoviral vectors essentially as described in Urnov et al. (2005) *Nature* 435(7042):646-651, Perez et al (2008) *Nature Biotechnology* 26(7): 808-816, and U.S. Patent Publication 2008/0131962.

The recognition helices for representative CXCR4 zinc-finger designs are shown below in Table 1. Exemplary ZFNs were targeted to exon 2 of the human CXCR4 gene, for example, to Proline-191 of the CXCR4 allele on human chromosome 2. Target sites of the CXCR4 zinc-finger designs are shown in the first column. Nucleotides in the target site that are contacted by the ZFP recognition helices are indicated in uppercase letters; non-contacted nucleotides indicated in lowercase. See, also, FIGS. 1A-C, showing the DNA sequence of the primary binding site for each ZFN as well as recognition helix sequences of each ZFN.

TABLE 1

CXCR4 Zinc-finger Designs

| ZFN Name | F1 | F2 | F3 | F4 | F5 |
|---|---|---|---|---|---|
| ZFN 12270<br>atGACTTGTGGGTGgttg<br>tgttccagtt<br>(SEQ ID NO: 1) | RSDSLLR<br>(SEQ ID<br>NO: 2) | RSDHLTT<br>(SEQ ID<br>NO: 3) | RSDSLSA<br>(SEQ ID<br>NO: 4) | DRSNLTR<br>(SEQ ID<br>NO: 5) | |
| ZFN 12273<br>ggGTAGAAGCGGTCac<br>agatatatctgt<br>(SEQ ID NO: 6) | DRSALSR<br>(SEQ ID<br>NO: 7) | RSDDLTR<br>(SEQ ID<br>NO: 8) | QSGNLAR<br>(SEQ ID<br>NO: 9) | QSGSLTR<br>(SEQ ID<br>NO: 10) | |
| ZFN 12257<br>agTCAGAGGCCAAGga<br>agctgttggctg<br>(SEQ ID NO: 11) | RSDTLSV<br>(SEQ ID<br>NO: 12) | DNSTRIK<br>(SEQ ID<br>NO: 13) | RSDNLAR<br>(SEQ ID<br>NO: 14) | QSADRTK<br>(SEQ ID<br>NO: 15) | |
| ZFN 12329<br>ttGGTGGCGTGGACGA<br>Tggccaggtagc<br>(SEQ ID NO: 16) | TSGNLTR<br>(SEQ ID<br>NO: 17) | DRSNLTR<br>(SEQ ID<br>NO: 5) | RSDALAR<br>(SEQ ID<br>NO: 18) | DRSHLSR<br>(SEQ ID<br>NO: 19) | TSGHLSR<br>(SEQ ID<br>NO: 20) |
| ZFN 12281<br>caGTTGATGCCGTGgc<br>aaactggtactt<br>(SEQ ID NO: 21) | RSDALSR<br>(SEQ ID<br>NO: 22) | DRSDLSR<br>(SEQ ID<br>NO: 23) | TSGNLTR<br>(SEQ ID<br>NO: 17) | TSGSLTR<br>(SEQ ID<br>NO: 24) | |
| ZFN 12290<br>ccAGAAGGGAAGCGtg<br>atgacaaagagg<br>(SEQ ID NO: 25) | RSDDLTR<br>(SEQ ID<br>NO: 8) | QSGNLAR<br>(SEQ ID<br>NO: 9) | RSDHLSA<br>(SEQ ID<br>NO: 26) | QSAHRIT<br>(SEQ ID<br>NO: 27) | |

K562 cells were transfected with either GFP or the indicated 2A-ZFN constructs with wild-type FokI using an Amaxa nucleofector (Lonza) and cultured for 3 days. Cells were then collected for genomic DNA preparation and subjected to a surveyor nuclease assay to measure the percentage of CXCR4 alleles modified (as assayed by the amount of NHEJ present in the pool) and the products analyzed on a 10% TBE polyacrylamide gel. All 3 pairs of ZFNs (2A-ZFN with wild-type FokI) are able to modify the human CXCR4 gene at relatively high efficiency (>20% NHEJ) (FIG. 1D).

Example 2

ZFN-Mediated Modification of the CXCR4

Engineered zinc-finger nucleases (ZFN) targeted to CXCR4 as described in Example 1 were used to generate novel CXCR4" SupT1 cell lines (SupX4⁻). As noted above, ZFNs have been used to stably disrupt endogenous genes in mammalian cells, including CCR5 in human lymphocytes, rendering them resistant to infection by R5 HIV-1 isolates (Miller et al. (2007) *Nat. Biotechnol.* 25:778-785; Perez et al. (2008) *Nat. Biotechnol.* 26:808-816 and U.S. Patent Publication 20080131962).

Figure 2A:
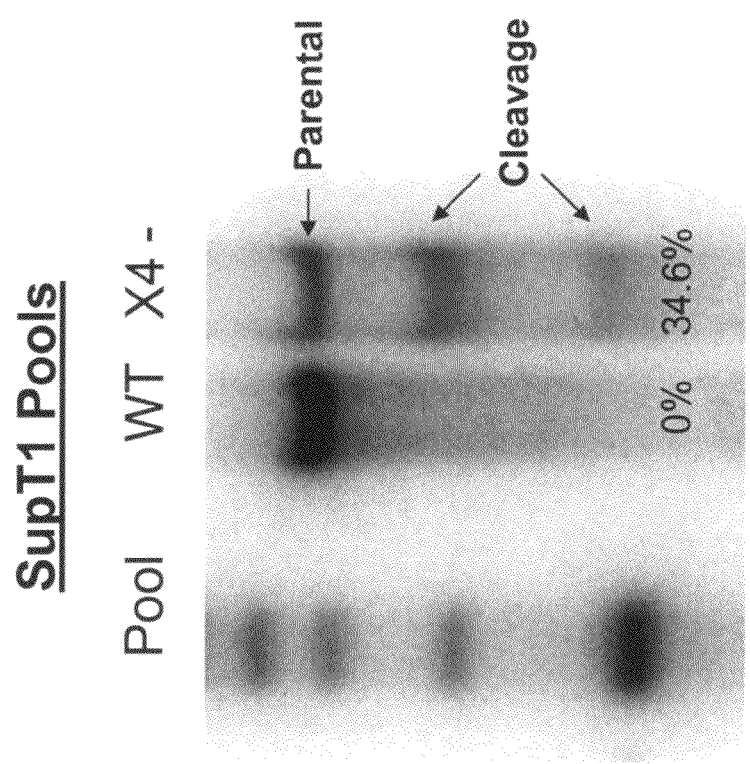
FIG. 2A is a gel showing the PCR amplified region of the CXCR4 gene targeted by ZFNs derived from the ZFN-enriched cell pool ($X4^-$) and wild-type (non-ZFN-treated) cells ("WT") and after treatment with the DNA mismatch-sensitive Surveyor Nuclease enzyme (Cel-1 assay). The percentage of alleles modified by ZFNs at the CXCR4 locus is shown beneath the two right-most lanes.

Constructs encoding a pair of CXCR4-targeted ZFNs (the 12273/12270 pair, 2A-ZFN with engineered FokI cleavage half-domains) were electroporated into SupT1 cells and cultured for 2 weeks. To enrich cells without surface CXCR4 expression, cells were first incubated with anti-CXCR4 mAb (12G5), washed, and then incubated with goat anti-mouse IgG conjugated with Dynal beads provided in the CELLection Pan mouse IgG kit (Invitrogen), followed by passing through a magnetic field. The enriched CXCR4⁻ SupT1 pool was maintained in RPMI-Complete medium and a portion of the cells were collected for genomic DNA preparation later. The genomic DNA was subjected to the Surveyor™ nuclease as described, for example, in U.S. Patent Publication Nos. 20080015164; 20080131962 and 20080159996, and the pool showed a 34.6% disruption in the CXCR4 allele (FIG. 2A).

The enriched CXCR4⁻ SupT1 pool was then used to generate single-cell derived clones by limiting dilution. A few single-cell derived clones were identified as CXCR4 knockout cell lines using a PCR-based screening and later confirmed to be lack of CXCR4 surface expression by flow cytometric analysis. Flow cytometry was conducted as follows: cells were first incubated with the indicated antibodies, washed, and then incubated with R-phycoerythrin (PE)-conjugated anti-mouse IgG before flow cytometric analysis.

As shown Table 2 below, CXCR4-ZFN modified clones showed similar profiles to the parental line, SupT1, with the exception of CXCR4 cell surface expression. Neither the X4 extracellular loop 2 (ECL2) directed antibody, 12G5, or the X4 amino-terminal (NT) antibody, 4G10, show reactivity.

TABLE 2

FACS evaluation of SupT1 clones treated with CXCR4-targeted ZFNs
FACS Evaluation of Sangamo's ZFN-CXCR4 SUPT1 Clones
(Mean Channel Fluorescence)

|  | Neg (P3) | Anti-CD4 (#19) | Anti-CXCR4 ECL2 (12G5) | Anti-CXCR4 NT (4G10) | Anti-HLA Cl-I W6/32 |
|---|---|---|---|---|---|
| SupT1 | 2 | 62 | 35 | 136 | 83 |
| Clone B4 | 2 | 114 | 2 | — | 152 |
| Clone B13 | 2 | 102 | 2 | 4 | 170 |
| Clone A66 | 4 | 92 | 3 | 7 | 189 |

Thus, SupT1 single cell-derived clones designated A66, B4, and B13 were identified to be CXCR4(−) based on lack of cell surface expression of CXCR4.

Furthermore, as determined by PCR-amplification and sequencing of genomic DNA, the resulting cells (clones) were confirmed to have all CXCR4 alleles disrupted by NHEJ, as shown in FIG. 2B and below in Table 3. As shown, one allele of the clone A66 has a 7 by deletion and a 2 by insertion (net 5 by deletion), the other allele has a 8 by deletion. One allele of the clone B4 has a 12 by deletion, the other allele has a 19 by deletion. The B13 clone has 3 different types of sequences: a 9 by deletion, a 29 by deletion, and a 54 by deletion.

TABLE 3

ZFN modifications in CXCR4

| Clone Designation | Modification in CXCR4 |
|---|---|
| A66 | 5 bp deletion (7 bp deletion and 2 bp insertion) |
|  | 8 bp deletion |
| B4 | 12 bp deletion |
|  | 19 bp deletion |
| B13 | 9 bp deletion |
|  | 29 bp deletion |
|  | 54 bp deletion |

Based on the genotype of each clone, the predicted amino acid sequences of CXCR4 expressed on SupT1 cells/clones is shown below (changes from wild-type shown in bold).

```
CXCR4 isoform b, WT (352 a.a.)
                                                     (SEQ ID NO: 28)
  1  MEGISIYTSD NYTEEMGSGD YDSMKEPCFR EENANFNKIF LPTIYSIIFL

51  TGIVGNGLVI LVMGYQKKLR SMTDKYRLHL SVADLLFVIT LPFWAVDAVA

101  NWYFGNFLCK AVHVIYTVNL YSSVLILAFI SLDRYLAIVH ATNSQRPRKL

151  LAEKVVYVGV WIPALLLTIP DFIFANVSEA DDRYICDRFY PNDLWVVVFQ

201  FQHIMVGLIL PGIVILSCYC IIISKLSHSK GHQKRKALKT TVILILAFFA

251  CWLPYYIGIS IDSFILLEII KQGCEFENTV HKWISITEAL AFFHCCLNPI

301  LYAFLGAKFK TSAQHALTSV SRGSSLKILS KGKRGGHSSV STESESSSFH

351  SS*

Clone #A66-seq1: 7 by deletion and 2 by insertion (272 a.a.)
                                                     (SEQ ID NO: 29)
  1  MEGISIYTSD NYTEEMGSGD YDSMKEPCFR EENANFNKIF LPTIYSIIFL

51  TGIVGNGLVI LVMGYQKKLR SMTDKYRLHL SVADLLFVIT LPFWAVDAVA

101  NWYFGNFLCK AVHVIYTVNL YSSVLILAFI SLDRYLAIVH ATNSQRPRKL

151  LAEKVVYVGV WIPALLLTIP DFIFANVSEA DDRYICDRFY PSVGGCVPVS

201  AHHGWPYPAW YCHPVLLLHY HLQAVTLQGP PEAQGPQDHS HPHPGFLRLL

251  AALLHWDQHR LLHPPGNHQA RV*

Clone #A66-seq2: 8 by deletion (189 a.a.)
                                                     (SEQ ID NO: 30)
  1  MEGISIYTSD NYTEEMGSGD YDSMKEPCFR EENANFNKIF LPTIYSIIFL

51  TGIVGNGLVI LVMGYQKKLR SMTDKYRLHL SVADLLFVIT LPFWAVDAVA

101  NWYFGNFLCK AVHVIYTVNL YSSVLILAFI SLDRYLAIVH ATNSQRPRKL

151  LAEKVVYVGV WIPALLLTIP DFIFANVSEA DDRYICDRF*

Clone #B4-seq1: 12 by deletion (348 a.a.)
                                                     (SEQ ID NO: 31)
  1  MEGISIYTSD NYTEEMGSGD YDSMKEPCFR EENANFNKIF LPTIYSIIFL

51  TGIVGNGLVI LVMGYQKKLR SMTDKYRLHL SVADLLFVIT LPFWAVDAVA

101  NWYFGNFLCK AVHVIYTVNL YSSVLILAFI SLDRYLAIVH ATNSQRPRKL

151  LAEKVVYVGV WIPALLLTIP DFIFANVSEA DDRYICDRFY PVVVFQFQHI

201  MVGLILPGIV ILSCYCIIIS KLSHSKGHQK RKALKTTVIL ILAFFACWLP
```

```
251  YYIGISIDSF ILLEIIKQGC EFENTVHKWI SITEALAFFH CCLNPILYAF

301  LGAKFKTSAQ HALTSVSRGS SLKILSKGKR GGHSSVSTES ESSSFHSS*
```

Clone #B4-seq3: 19 by deletion (283 a.a.)

(SEQ ID NO: 32)

```
  1  MEGISIYTSD NYTEEMGSGD YDSMKEPCFR EENANFNKIF LPTIYSIIFL

51  TGIVGNGLVI LVMGYQKKLR SMTDKYRLHL SVADLLFVIT LPFWAVDAVA

101  NWYFGNFLCK AVHVIYTVNL YSSVLILAFI SLDRYLAIVH ATNSQRPRKL

151  LAEKVVYVGV WIPALLLTIP DFIFANVSEA DDRYILTCGW LCSSFSTSWL

201  ALSCLVLSSC PAIALSSPSC HTPRATRSAR PSRPQSSSSW LSSPVGCLTT

251  LGSASTPSSS WKSSSKGVSL RTLCTSGFPS PRP*
```

Clone #B13: 9 by deletion (349 a.a.)

(SEQ ID NO: 33)

```
  1  MEGISIYTSD NYTEEMGSGD YDSMKEPCFR EENANFNKIF LPTIYSIIFL

51  TGIVGNGLVI LVMGYQKKLR SMTDKYRLHL SVADLLFVIT LPFWAVDAVA

101  NWYFGNFLCK AVHVIYTVNL YSSVLILAFI SLDRYLAIVH ATNSQRPRKL

151  LAEKVVYVGV WIPALLLTIP DFIFANVSEA DDRYICDRFY LWVVVFQFQH

201  IMVGLILPGI VILSCYCIII SKLSHSKGHQ KRKALKTTVI LILAFFACWL

251  PYYIGISIDS FILLEIIKQG CEFENTVHKW ISITEALAFF HCCLNPILYA

301  FLGAKFKTSA QHALTSVSRG SSLKILSKGK RGGHSSVSTE SESSSFHSS*
```

Clone #B13-seq2: 29 bp-deletion (264 a.a.)

(SEQ ID NO: 34)

```
  1  MEGISIYTSD NYTEEMGSGD YDSMKEPCFR EENANFNKIF LPTIYSIIFL

51  TGIVGNGLVI LVMGYQKKLR SMTDKYRLHL SVADLLFVIT LPFWAVDAVA

101  NWYFGNFLCK AVHVIYTVNL YSSVLILAFI SLDRYLAIVH ATNSQRPRKL

151  LAEKVVYVGV WIPALLLTIP DFIFANVSEA DDRYICGCVP VSAHHGWPYP

201  AWYCHPVLLL HYHLQAVTLQ GPPEAQGPQD HSHPHPGFLR LLAALLHWDQ

251  HRLLHPPGNH QARV*
```

Clone #B13-seq3: 54 by deletion (334 a.a.)

(SEQ ID NO: 35)

```
  1  MEGISIYTSD NYTEEMGSGD YDSMKEPCFR EENANFNKIF LPTIYSIIFL

51  TGIVGNGLVI LVMGYQKKLR SMTDKYRLHL SVADLLFVIT LPFWAVDAVA

101  NWYFGNFLCK AVHVIYTVNL YSSVLILAFI SLDRYLAIVH ATNSQRPRKL

151  LAEKVVYVGV WIPALLLTIP DFIFANVSEA VQFQHIMVGL ILPGIVILSC

201  YCIIISKLSH SKGHQKRKAL KTTVILILAF FACWLPYYIG ISIDSFILLE

251  IIKQGCEFEN TVHKWISITE ALAFFHCCLN PILYAFLGAK FKTSAQHALT

301  SVSRGSSLKI LSKGKRGGHS SVSTESESSS FHSS*
```

SupT1 cells are quadraploid, but generally have only 2 copies of chromosome 2 and 9. Therefore, the presence of 3 different types of sequences in clone B13 suggests that either the clone B13 has 3 CXCR4 alleles or it is a mixed clone. In any case, both CXCR4 surface staining and sequence analysis indicated that clone B13 is a CXCR4 knock-out clone.

Example 3

ZFN-Mediated Modification of CXCR4 Prevents Infection by CXCR4-Tropic and Dual-tropic HIV Strains To evaluate the response to viral challenge, SupT1 and clones B13 and A66 were plated at $1.0 \times 10^6$ cells/ml and spin-infected for 1 hour at 1,500 rpm. Cell culture supernatants were collected over the course of 3 weeks to measure HIV-1 reverse transcriptase (RT) activity.

Figure 3:
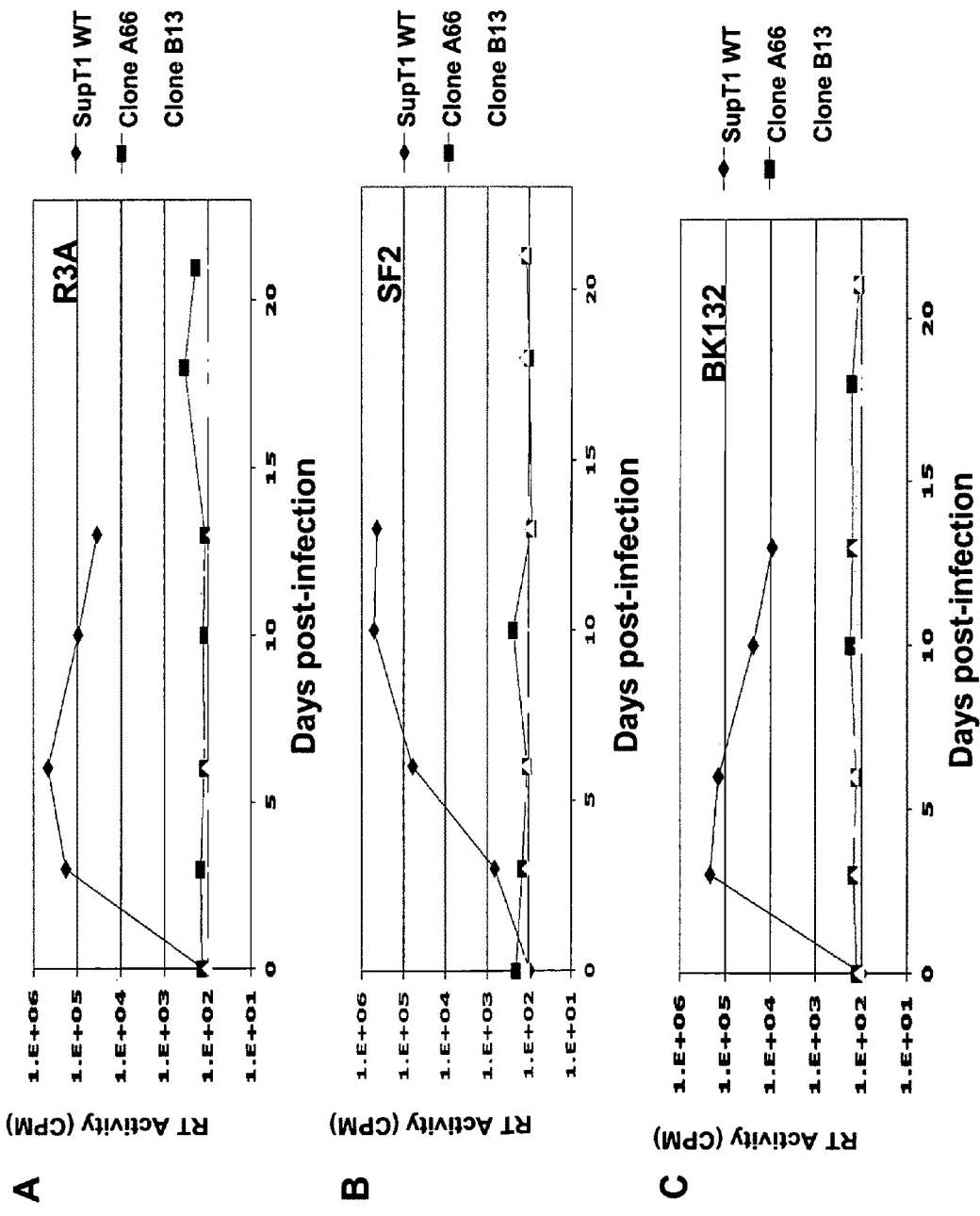
FIG. 3, panels A to C, are graphs depicting infection of wild-type SupT1 and CXCR4 SupT1 modified clones B13 and A66.

As shown in FIGS. 3A-3C, the CCR5/CXCR4 (R5/X4) dual tropic viruses HIV-1 R3A and SF2 are able to productively infect parental SupT1 cells but were not able to infect the SupT1 clones B13 or A66 (FIGS. 3A and 3B). SupT1 cells do not normally express CCR5 and thus are not susceptible to R5-tropic HIV strains or to R5/X4 tropic viruses utilizing CCR5 for entry. FIG. 3C shows the same selectivity for the strictly X4 tropic HIV-1 BK132 virus.

Thus, ZFN disruption of the CXCR4 gene in B13 and A66 clones renders them resistant to CXCR4 tropic virus infection.

Furthermore, as shown by flow cytometric analysis above (Table 2), the resistance of clone A66 and B13 to HIV-1 infection is due to ZFN-mediated modification of the endogenous CXCR4 gene. As shown in Table 2, cell surface expression of CD4 and HLA Class I on clone A66 and B13 were examined and slightly higher levels of CD4 and HLA expression were detected in clone A66 and B13, indicating that the resistance of clone A66 and B13 to HIV-1 infection is not related to CD4 and HLA Class I expression on these cells.

Furthermore confirmation that the resistance of SupT1 clones to HIV-1 infection is due to ZFN-mediated genome modification at the CXCR4 locus was obtained by transducing clones B13 and A66 with either CXCR4- or CCR5-containing pELNS replication-defective lentiviral vector, generated as previously described in Richardson et al. (2008) *J. Virol.* 82:11117-11128). These transduced cell populations were used to generate stable cell lines and then challenged with HIV-1 to test whether the susceptibility of these cells to HIV-1 infection can be restored. Cells were stained with the indicated antibody and analyzed using a flow cytometer. As shown in Table 5, numbers shown are mean fluorescence intensity (MFI) for each condition.

TABLE 5

Flow cytometric analysis of SupT1 cells and the ZFN modified SupT1 clones

|  | SupT1 | B13 | B13-X4 | A66-X4 |
| --- | --- | --- | --- | --- |
| Anti-CXCR4 | 78.7 | 4.4 | 33.7 | 105.5 |
|  | SupT1-R5 | B13 | B13-R5 | A66-R5 |
| Anti-CCR5 | 30.8 | 8.1 | 22.6 | 29.6 |

Thus, transduction with CCR5 expression vectors can cause the B13 and A66 cell lines to express CCR5 on the surfaces (see B13R5 and A66R5 respectively).

In addition, SupT1 stably expressing CCR5 (SupT1-R5), B13, B13-X4 were plated at $1 \times 10^6$ cells/ml and spin-infected with the R5/X4 dual-tropic HIV-1 strain R3A for 1 hour at 1,500 rpm. Cell culture supernatants were collected over the course of 3 weeks to determine the relative amount of HIV replication in the culture by measuring the level of HIV-1 reverse transcriptase (RT) activity in the media.

Figure 4:
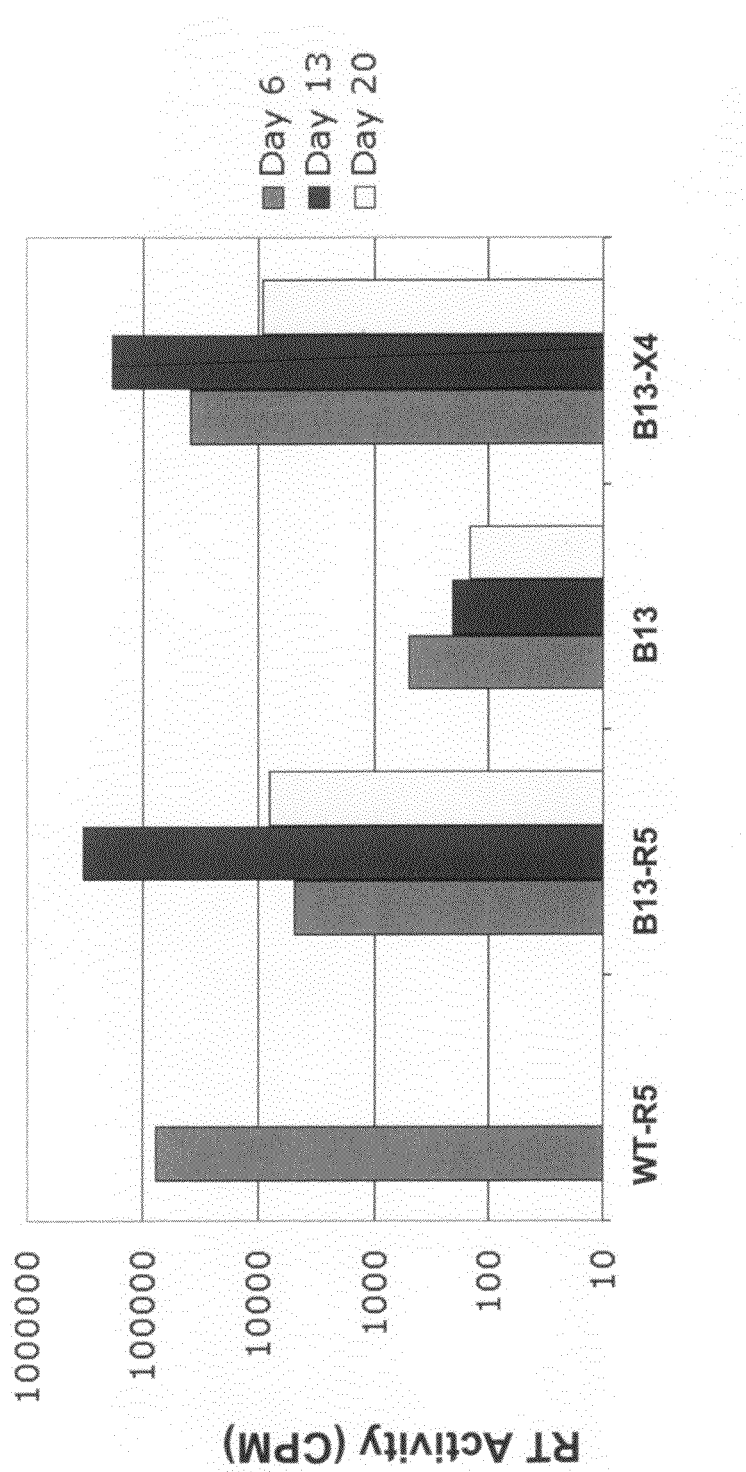
FIG. 4 is a graph depicting Reverse Transcriptase (RT) activity following R3A (a CCR5/CXCR4, also referred to as R5/X4, trophic HIV-1 virus) challenge with the indicating cell types. The left most bar shows RT activity 6 days after challenge; the middle bar shows RT activity 13 days after challenge and right bar shows RT activity 20 days after challenge. This demonstrates that B13 cells are resistant to HIV due to the disruption of CXCR4 by the CXCR4-specific ZFNs as re-introduction of either CCR5 or CXCR4 restores infectivity back to wild-type levels when using the R5/X4 tropic HIV strain.

As shown in FIG. 4, the dual tropic (R5/X4) HIV-1 R3A was able to productively infect both the B13 transfectants stably expressing either CXCR4 (B13-X4), or CCR5 (B13-R5) on their surface but not the parental B13 clone. Thus, the absence of virus replication is due exclusively to the absence of CXCR4 on the cell surface and not a general defect in the SupT1 B13 clone.

Example 4

CXCR4-Specific Modification of Primary T Cells

To investigate whether the CXCR4-specific ZFNs would have the same protective affect on primary T cells, the following experiments were done.

Fresh CD4+ T cells from live human donors were obtained from the Human Immunology Core at the University of Pennsylvania. 2.5 million CD4+ T cells were seeded at a density of $0.8 \times 10^6$ in RPMI containing 10% fetal calf serum, 1% penicillin/streptomycin, and 100 U/ml interleukin-2. The cells were stimulated with anti-CD3/anti-CD28 coated magnetic beads (for example, Dynal) at a 3:1 bead to cell ratio. Approximately 18 hrs post-stimulation, the cells were transduced with an Ad5/F35 vector encoding either the CXCR4-specific ZFN pair as described in Example 2 or a CCR5-specific ZFN pair (see US Patent Publication 20080159996) at a multiplicity of infection (moi) of 600. As a control, an untransduced culture was maintained throughout.

Beginning 72 hours post-stimulation cells were counted every 48 hours with a Coulter Counter Multisizer 3 and split to $0.8 \times 10^6$ with fresh media containing 100 U/ml IL-2. The CXCR4-ZFN treated pools were examined by the Surveyor™ nuclease assay as described, for example, in U.S. Patent Publication Nos. 20080015164; 20080131962 and 20080159996, and the data is presented in FIG. 5 (mock-infected samples). These data indicate that the CXCR4-specific ZFNs were able to specifically modify the CXCR4 locus at efficiencies of greater than 40 percent, whereas, as expected, cells treated with the CCR5-specific ZFNs showed no modification at the CXCR4 locus.

Figure 6:
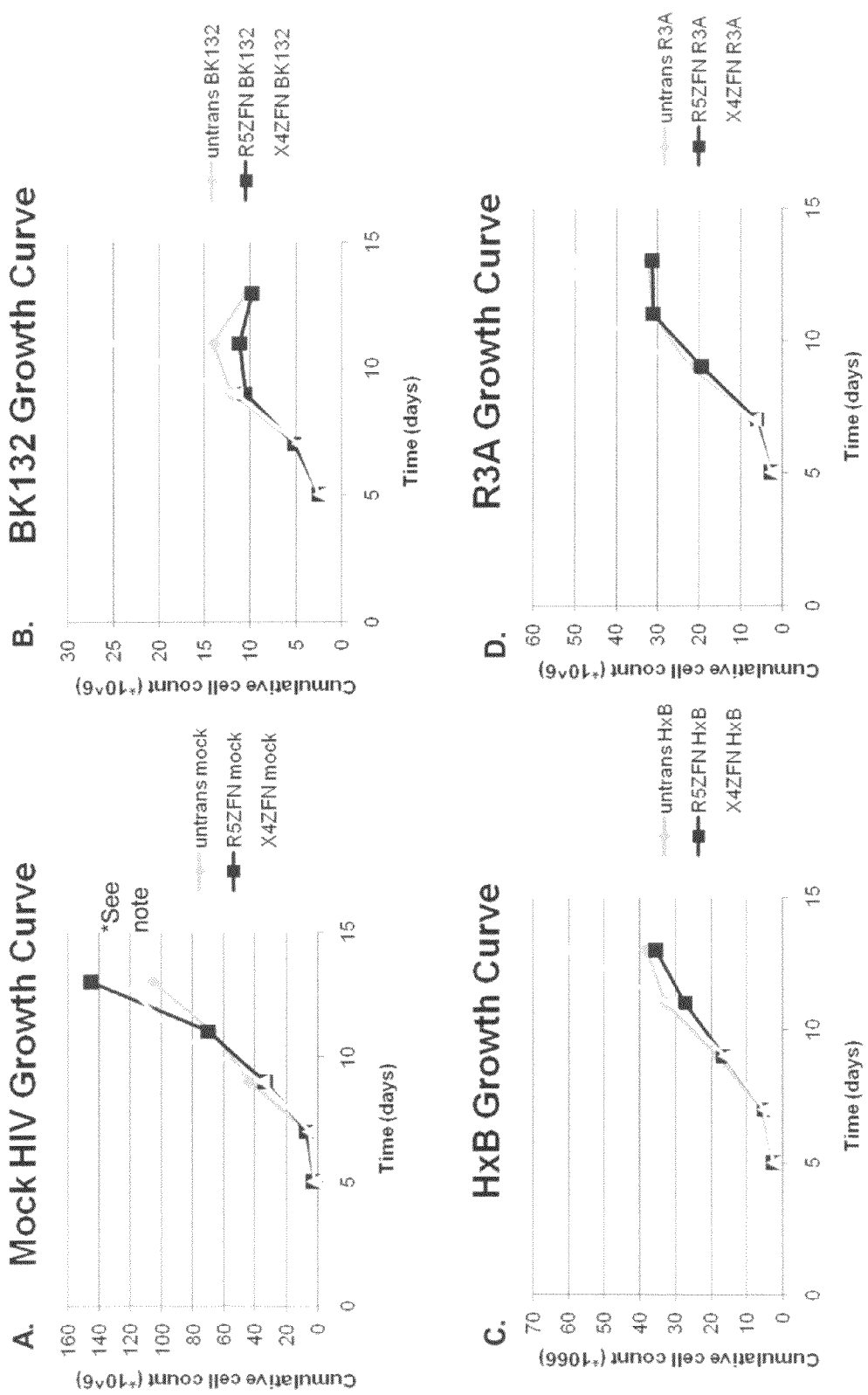
FIG. 6, panels A to D, are graphs depicting the protective effect offered by treatment of primary T cells with CXCR4-specific ZFNs. Cells were treated with CXCR4-specific or CCR5-specific ZFNs and then infected with strains of HIV with varying degrees of CXCR4 tropisms.
Figure 7:
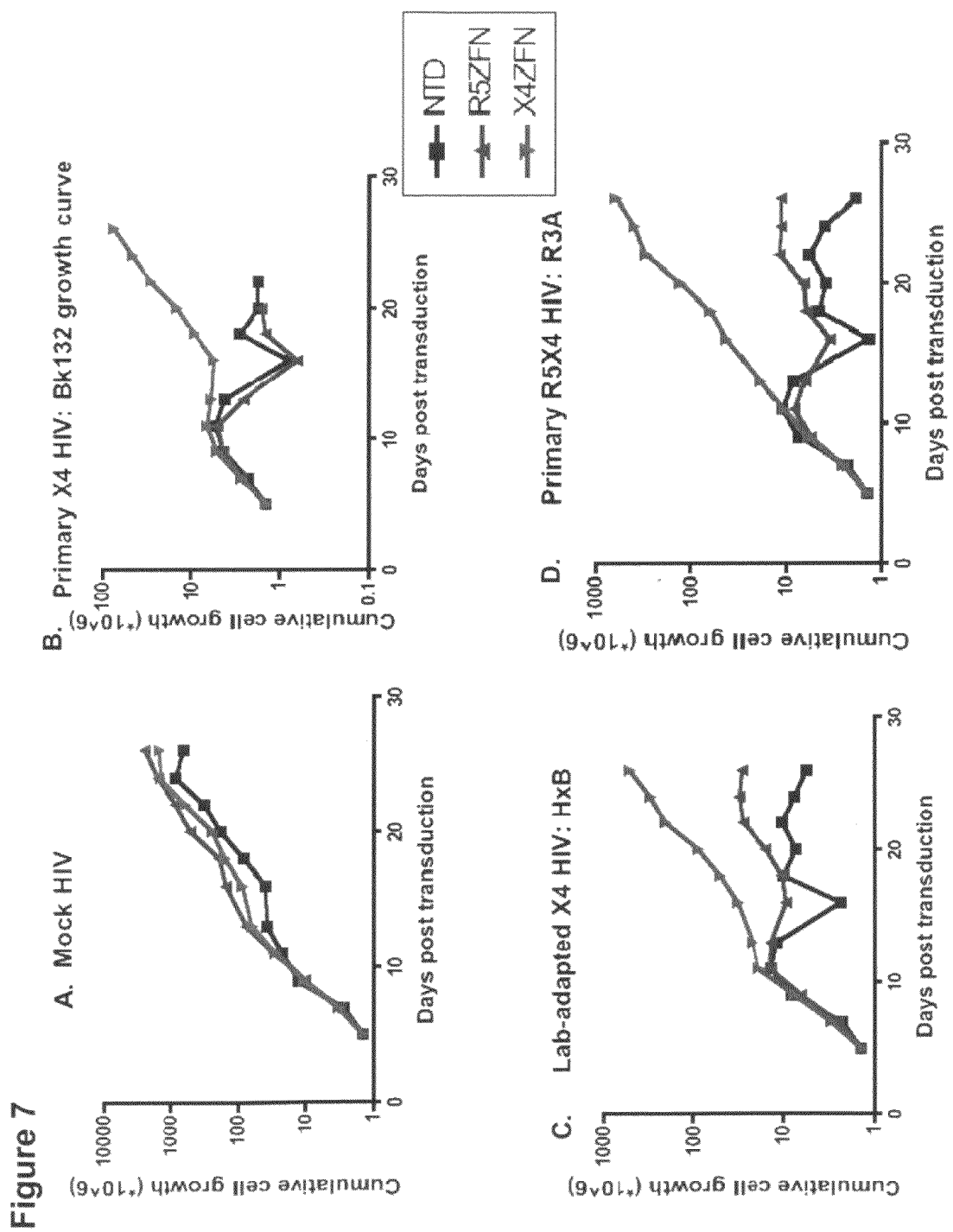
FIG. 7, panels A to D, are graphs depicting the protective effect offered by treatment of primary T cells with CXCR4-specific ZFNs. Cells were treated with CXCR4-specific or CCR5-specific ZFNs and then infected with CXCR4 tropic or R5/X4 tropic HIV strains.

Five days post-stimulation the anti-CD3/anti-CD28 coated magnetic beads were removed from each of the three cultures (NTD, AdX4-ZFN, and AdR5-ZFN) and 2.5 million cells were seeded in each of four cultures that were subsequently infected with various HIV strains. The strains used were either Bk132 (primary CXCR4-tropic isolate), HxB2 (lab-adapted CXCR4-tropic isolate), and R3A (CCR5/CXCR4-dual tropic primary isolate). A mock infection culture was maintained as well. A dose of 100 ng p24 of HIV was used per million cells. The data are presented in FIG. 6, where it is evident that the CXCR4-tropic HIV strains were less lethal to those cells that had been treated with the CXCR4-specific ZFNs. The cultures were monitored for an additional 15 days for a total of 30 days, and these data are presented in FIG. 7.

Figure 5:
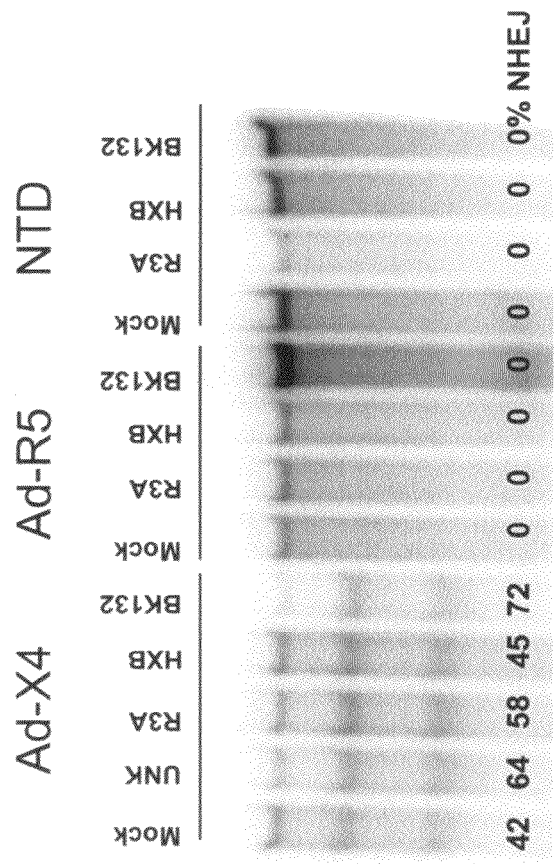
FIG. 5 depicts a gel showing the frequency of non-homologous end joining (NHEJ) events in primary T cells treated with CXCR4-specific ZFNs as assayed by Surveyor™ nuclease assay.

Eight days post infection with the different HIV strains, cells were harvested and analyzed for CXCR4 expression by FACS. Briefly, cells were harvested by centrifugation at 1500 rpm for 5 minutes and washed with FACS buffer (FB: 1 L PBS, 25 mL FCS (GIBCO), 2 mL 0.5 M EDTA). The cells were then stained for 20 minutes with anti-CXCR4-APC monoclonal antibody (Becton Dickinson) using 5 uL per 1 million cells in 100 uL FB at room temperature. Cells were washed with FB, and then permeabilized for 20 minutes with 100 uL of Caltag A™ (InVitrogen) at room temperature. Cells were then washed again with FB. The cells were then stained for HIV Gag using 2 uL/million cells of KC57-RD1 (Beckman Coulter) in 100 uL of Caltag™ B for 30 minutes at room temperature. Cells were washed and resuspended in 250 uL of FB. All samples were run on a LSRII (BD) and analyzed with FlowJo 8.0.1 software. Cells treated with the CXCR4-specific ZFNs were much less sensitive to CXCR4-tropic HIV strains. In addition, an enrichment (increased survival and/or proliferation) of CXCR4-specific ZFN-modified cells was already noticeable in Ad-X4 ZFN-treated samples infected with BK132 and R3A, based on the increased percentage of CXCR4 alleles modified by NHEJ frequency in these samples compared with the uninfected control sample (mock) as illustrated in FIG. 5.

In addition, these cells were analyzed by 454 deep sequencing in the presence or absence of HIV exposure. Genomic DNA was isolated from CD4+ T cells using QIAamp DNA Micro Kit (Qiagen). For each condition, 200 ng genomic DNA was then PCR amplified using Platinum Taq High Fidelity (Invitrogen). The following primers plus the 454 adaptor sequences and 8 letter DNA barcodes were used: CAACCTCTACAGCAGTGTCCTCATC (forward) (SEQ ID NO:36) and GGAGTGTGACAGCTTGGAGATG (reverse) (SEQ ID NO:*37) At 95° for 5 min, then 30 cycles of 95° for 30 sec, 55° for 3 sec, 68° for 30 sec, followed by 68° for 2 min.

Following PCR amplification, the PCR product was analyzed on a 2% agarose gel and then extracted and gel purified using Wizard SV Gel and PCR Clean-Up System (Promega). Quant-iT dsDNA High-Sensitivity Assay Kit (Invitrogen) was then used to determine the concentration of each bar coded amplicon. DNA samples were then pooled at an equimolar ratio and run on a Roche/454 GS FLX using standard chemistries at the University of Pennsylvania DNA Sequencing Facility. Results were analyzed by first separating the sequence reads by barcode and then aligning each sequence read to the expected wild-type genomic sequence. Insertions or deletions consistent with ZFN-induced NHEJ events were flagged automatically and confirmed by manual inspection.

Figure 8:
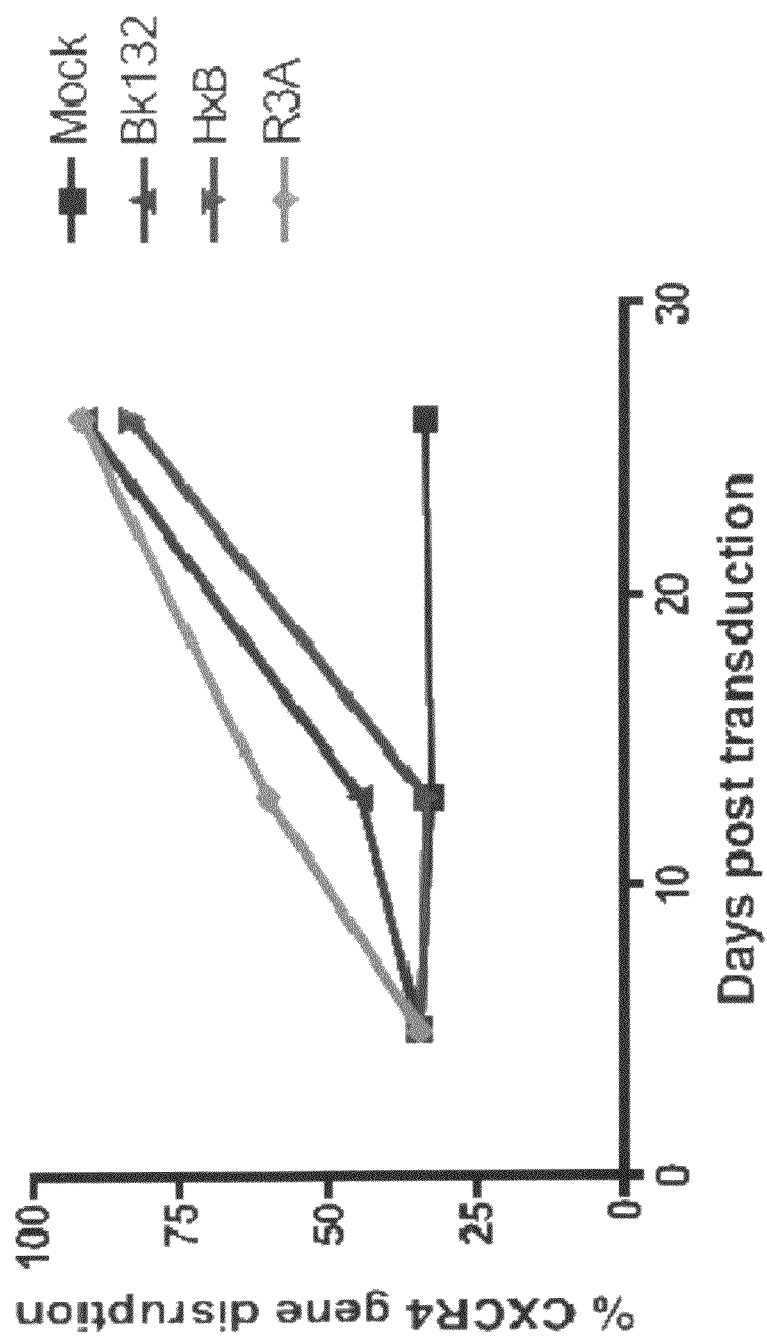
FIG. 8 is a graph depicting the percent of CXCR4 gene disruption measurable in primary T cells following exposure to HIV strains in vitro. In the absence of HIV exposure (Mock) the percent CXCR4 gene modification remains fairly constant. When the cells are exposed to CXCR4-tropic HIV (either a natural CXCR4 strain, Bk132 or a laboratory modified CXCR4 strain, HxB) the percent of CXCR4 modification increases indicating that the CXCR4 modification provides a survival advantage to those cells that have CXCR4 modified. Given the level of disruption detected by direct sequencing exceeds 75% of all alleles in the cell population, cells with both copies of CXCR4 disrupted are selected for and proved the most robust protection against HIV.

As shown in FIG. 8, in the absence of HIV exposure (labeled "mock" in FIG. 8), the percentage of disrupted CXCR4 alleles is steady over time. In contrast, in the presence of either the natural CXCR4 tropic HIV strain (Bk132) or the lab adapted CXCR4-tropic HIV strain (HxB), the percent of CXCR4 gene disruption in the population increases, presumably due to the disruption of CXCR4 blocking the ability of X4-tropic viruses to infect these cells and conferring a survival advantage to the cell population modified by the CXCR4-specific ZFNs.

These primary T cells were also analyzed to determine the viral load present in the culture over time following treatment with either CXCR4-specific ZFNs or CCR5-specific ZFNs. Fresh CD4+ T cells from live human donors, purified by negative selection, were obtained from the Human Immunology Core at the University of Pennsylvania. 2.5 million CD4+ T cells were seeded at a density of $0.8 \times 10^6$ in RPMI containing 10% fetal calf serum, 1% penicillin/streptomycin, and 100 U/ml interleukin-2. The cells were stimulated with anti-CD3/anti-CD28 coated magnetic beads at a 3:1 bead to cell ratio.

Approximately 18 hrs post-stimulation, the cells were transduced with an Ad5/F35 vector encoding either the X4-ZFN or R5-ZFN as described above in Example 4 at a multiplicity of infection (moi) of 600. An untransduced culture was maintained throughout. Beginning 72 hours post-stimulation cells were counted every 48 hours using trypan blue dye exclusion on an automated hemocytometer (Countess, Invitrogen) and split to $0.8 \times 10^6$ with fresh media containing 100 U/ml IL-2.

Five days post-stimulation the anti-CD3/anti-CD28 coated magnetic beads were removed from each of the three cultures (NTD, AdX4-ZFN, and AdR5-ZFN) and 2.5 million cells were seeded in each of four cultures that were subsequently infected with either Bk132 (primary X4 isolate), HxB2 (lab-adapted X4 isolate), R3A (R5X4 primary isolate), or media only (mock). A dose of 100 ng p24 of HIV was used per million cells. Cells were then expanded until growth plateaued, and then cells were restimulated with anti-CD3/anti-CD28 beads for an additional 3 days. Cultures were then maintained until growth plateaued again approximately 26 days after the initial stimulation.

Reverse transcriptase activity was determined for each culture approximately every two days post HIV infection. An aliquot of 1.25 mL of each cell culture was spun in a sterile FACS tube at 1500 rpm for 5 min. Then, 1 ml of cell-free supernatant was transferred to a 1.5 ml ultracentrifuge tube and pelleted at 45,000 rpm for 30 min at 4 degrees. Supernatant was aspirated and viral pellets were resuspended in 50 ul of 0.25M Tris pH 8.0. 50 uL of solubilizing buffer (0.8M NaCl, 0.5% Triton X-100, 20% glycerol, 0.05M Tris pH7.9, 1 mM DTT) was added and then incubated for 10 min. 20 uL was then aliquoted to each of two glass tubes and 79.2 ul RT cocktail (67.5 mM Tris pH7.5, 1.35 mM DTT, 1.08 mM ATP, 13.5 mM MgCl2), 5 ul poly r(A) (10 units/ml), 0.3 uL 3HdTTP (1 mCi), and 0.125 ul cold dTTP was added to each tube. Tubes were then incubated with slow shaking at 37 degrees for 1 hour. Tubes were placed on ice and 20 uL of tRNA (11.3 mg/ml) and 2 mL of cold 10% TCA with pyrophosphate was added. Each sample was then poured through a vacuum manifold onto a glass filter. The filter was then washed three times with 5% TC and once with 100% ethanol. The filter was then placed in scintillation vial with 3 mL of scintillation cocktail. Activity was measured on a scintillation counter. Reverse transcriptase activity was then normalized to the live cell number at each time point.

Figure 9:
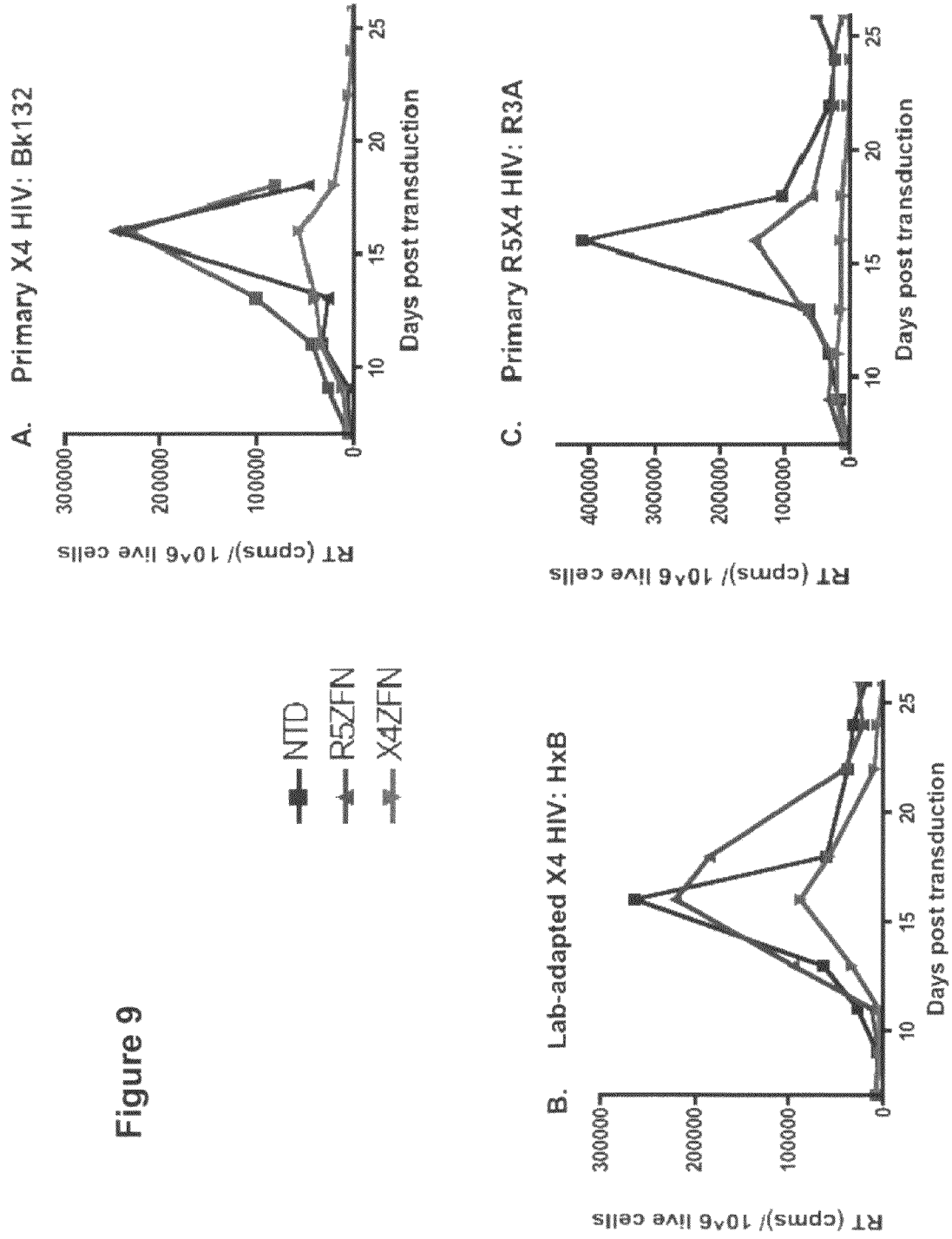
FIG. 9, panels A to C, are graphs depicting viral load as measured by reverse transcriptase (RT) activity, in samples that had either been treated with CXCR4-specific or CCR5-specific ZFNs. The indicated cells were treated with the ZFNs and then exposed to either CXCR4-tropic HIV strains (Bk132 as shown in FIG. 9A; HxB as shown in FIG. 9B) or an HIV strain exhibiting dual tropism for both CCR5 and CXCR4 (R5X4 shown in FIG. 9C). In all data presented, the amount of RT activity was highest in either the non treated samples (NTD) or in the samples that had been treated with CCR5-specific ZFNs and exposed to CXCR4-tropic HIV strains.

As shown in FIG. 9 primary T cells treated with CXCR4-specific ZFNs (see FIG. 9, 'X4ZFN') and exposed to a natural CXCR4-tropic HIV (Bk132) or a lab adapted CXCR4-tropic HIV strain (HXB) had a decreased amount of viral load in comparison with cells treated with CCR5-specific ZFNs or mock infected cells.

Example 5

In vivo Challenge of Mice Engrafted with Human CD4+ T Cells

To determine the resistance of the ZFN treated T cells to CXCR4 tropic HIV strains in vivo, human CD4+ T cells were engrafted into NSG mice. 25 million human CD4+ T cells were stimulated as previously described and then transduced with either AdR5-ZFN or AdX4-ZFN (as described in Example 4) at an MOI of 600. Cells were maintained as previously described during 10 days of in vitro expansion. The day of injection, the cells were pelleted for 5 min at 1500 rpm and then resuspended at 10^8 cells/ml in PBS.

One hundred ul of cells ($10^6$ cells per mouse) were then injected via the tail vein into each NSG mouse. Twenty-three mice received injections of X4-ZFN treated cells, and 22 mice received injections of R5-ZFN cells. Twenty seven days post-injection diagnostic retroorbital bleeds were performed on each mouse. To determine CD4 counts, 50 ul of whole blood was then stained in a Trucount tube (BD) for 20 minutes at room temperature with 2.5 ul anti-CD45 FITC (BD), 0.5 ul anti-CD3 Qdot655 (Invitrogen), 2.5 ul anti-CD4 alexa fluor 700 (BD), 1 ul anti-CD8 pacific blue (Biolegend), and 5 ul anti-CXCR4 PE (BD). Red blood cells were then lysed and samples were fixed with 1×FACS Lysing solution (BD). Cells were then run on an LSRII flow cytometer. Data was then analyzed with FlowJo 8.8.6 software. CXCR4 gating was determined with a fluorescence minus one control on human whole blood. Unpaired student t-tests were then performed to compare engraftment and CXCR4 expression between groups. Prism was used for all statistical analysis (GraphPad Software, Inc.).

Figure 10:
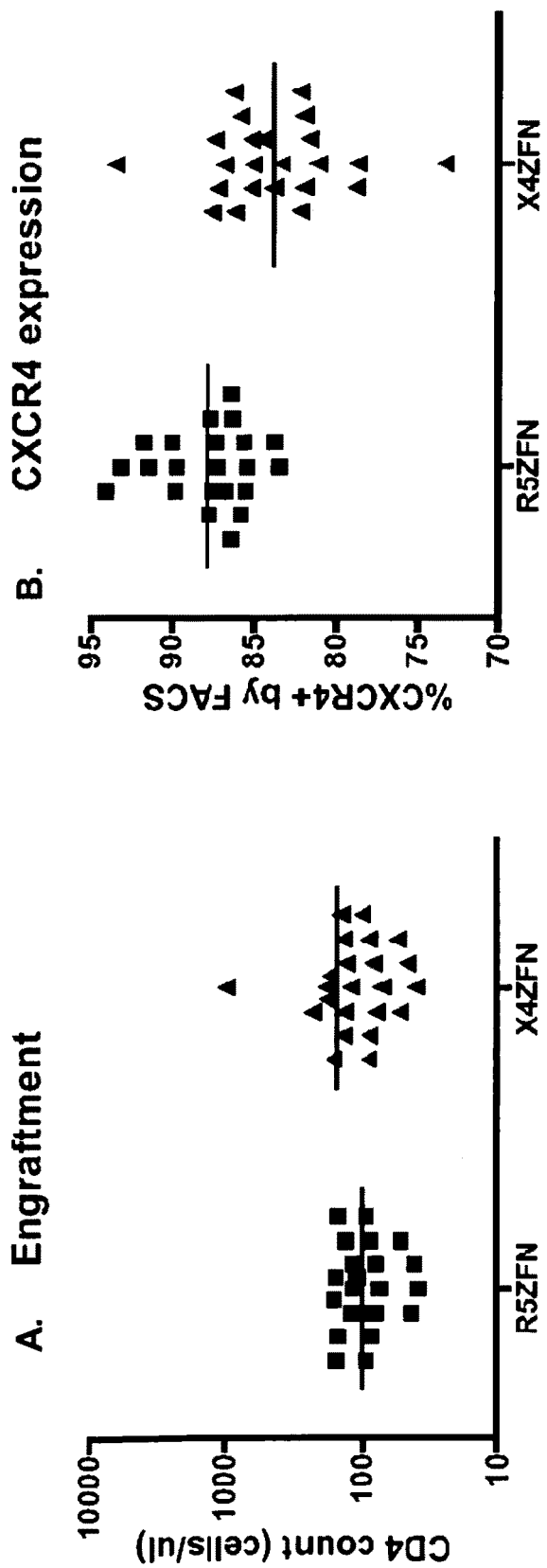
FIG. 10, panels A and B, are graphs depicting engraftment of the ZFN treated human T cells in NSG mice and the percent of CXCR4 surface expression in the ZFN treated cells.

As shown in FIG. 10, there was no difference in engraftment between the cells treated with either the CXCR4-specific ZFNs or the CCR5-specific ZFNs as measured 27 days post implantation (see FIG. 10A). In addition, the level of CXCR4 expression was measured by FACS analysis (described above) in the engrafted cells, and as expected, the amount of CXCR4 expression was less in the mice that had received cells that had been treated with the CXCR4-specific ZFNs (FIG. 10B).

To HIV infect the mice, $10^5$ autologous HIV-infected CD4+ T cells were injected in the tail vein of each mouse in 100 ul total volume. The cells were previously stimulated with anti-CD3/anti-CD28 beads for 5 days and then HIV infected with 100 ng p24 Bk132 per million cells or mock infected for four days. Alternatively, HIV infection was initiated in the mice by injecting them with HIV-infected PBMC. After four days of HIV infection, the cells were frozen and stored in liquid nitrogen until being thawed four hours before injection. For both the R5-ZFN and X4-ZFN groups, 11 mice received HIV-infected cells, and 11 mice received mock-infected cells. Notably, one mouse injected with X4-ZFN modified cells had engraftment >4 standard deviations from the mean and was thus not included in the HIV challenge phase of the experiment.

After HIV infection, diagnostic bleeds were conducted every 7 days to analyze CD4 counts, viral load, and CXCR4 expression. Spleen and bone marrow tissues were collected for analysis of CXCR4 expression. In addition, the percent of CXCR4 gene modification was analyzed by Cel-1 analysis using the Surveyor™ assay as described above, and the preliminary data are presented below in Table 6. As can be seen in the Table, in some mice, the presence of the HIV infection may cause an increase in the percent of CXCR4 modification in the tissue (compare mouse 6073 with 6069 for example).

TABLE 6

Preliminary analysis of CXCR4 expression in HIV challenged mice

| Mouse | Cells used for viral infection | HIV challenge | Tissue type | % CXCR4 modification |
|---|---|---|---|---|
| 6075 | PBMC | mock | blood | 18.60 |
| 6075 | PBMC | mock | spleen | 20.20 |
| 6075 | PBMC | mock | bone marrow | NC |
| 6081 | PBMC | HIV | blood | 15.30 |

TABLE 6-continued

Preliminary analysis of CXCR4 expression in HIV challenged mice

| Mouse | Cells used for viral infection | HIV challenge | Tissue type | % CXCR4 modification |
|---|---|---|---|---|
| 6081 | PBMC | HIV | spleen | 2.50 |
| 6081 | PBMC | HIV | bone marrow | NC |
| 6073 | CD4 | HIV | blood | 37.70 |
| 6073 | CD4 | HIV | spleen | 59.90 |
| 6073 | CD4 | HIV | bone marrow | 59.50 |
| 6069 | CD4 | mock | blood | 36.00 |
| 6069 | CD4 | mock | spleen | 24.90 |
| 6069 | CD4 | mock | bone marrow | 29.70 |
| 6079 | CD4 | HIV | blood | 18.20 |
| 6079 | CD4 | HIV | spleen | 8.50 |
| 6079 | CD4 | HIV | bone marrow | NC |

Note:
"NC" denotes results that were non-conclusive.

In sum, sequencing of CXCR4 in all ZFN-modified cell lines demonstrated disruption of the DNA at the ZFN target site characterized by a variety of deletions or insertions resulting in frameshift, premature termination, and amino acid mutations. While the control SupT1 cell line remained highly sensitive to CXCR4 tropic and R5X4 tropic HIVs, ZFN-modified lines were completely resistant to infection by several HIV-1 isolates including HXB and R3A, as determined by RT activity, PCR, and immunofluorescence microscopy. Moreover, in cultures containing mixtures of ZFN-treated and control SupT1 cells in ratios as low as 1:1000, ZFN-treated cells showed preferential survival in the setting of a cytopathic X4 virus infection. ZFN-modified cells exhibited no differences in growth kinetics and became fully permissive to R5-tropic HIV infection when re-engineered to stably express CCR5. In addition, the data demonstrate that the CXCR4-specific ZFNs were able to offer protection in primary T cells against CXCR4-tropic HIV strains.

These data demonstrate that ZFNs can be successfully designed to disrupt the CXCR4 gene resulting in resistance to CXCR4-dependent HIV infection.

Example 6

ZFN-Modification of CXCR4 and CCR5 in Primary T-cells

Figure 11:
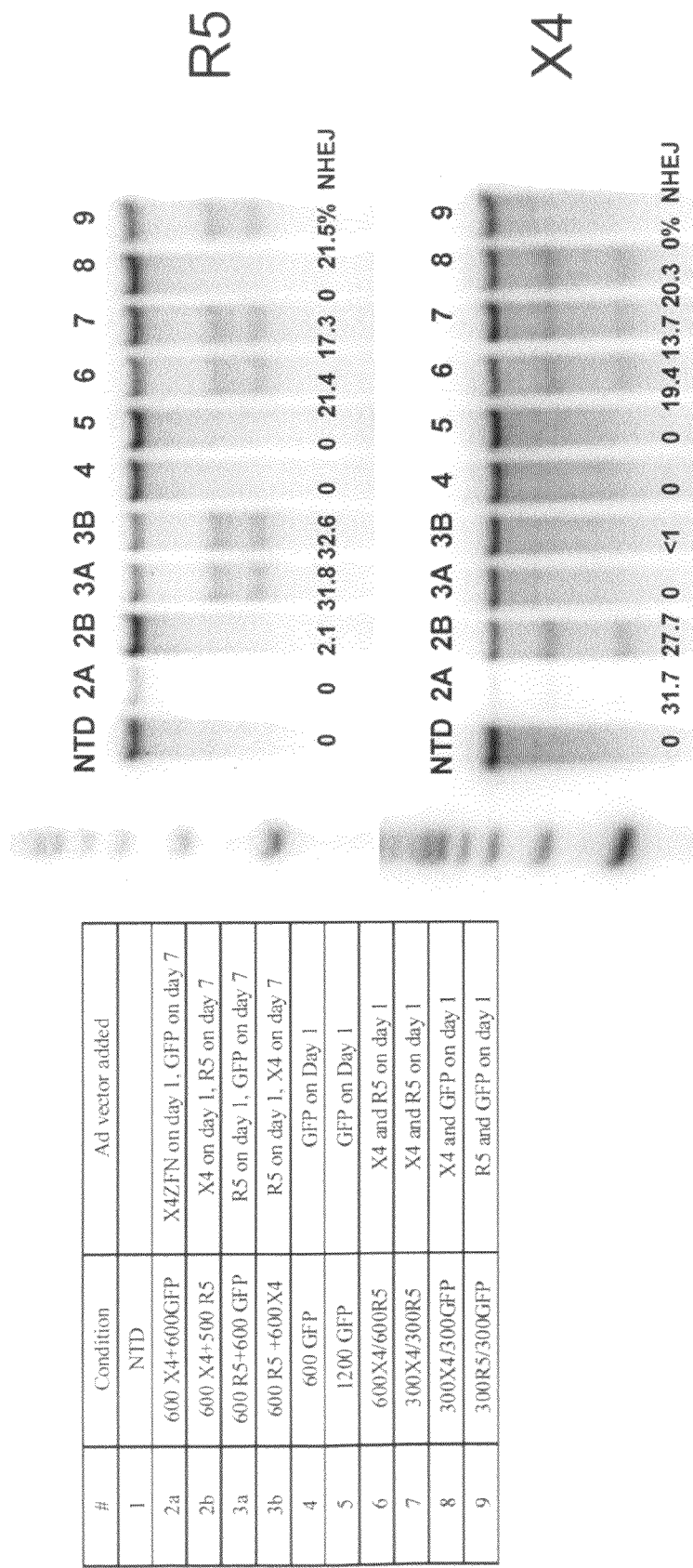
FIG. 11 depicts gels showing the frequency of non-homologous end joining (NHEJ) events in primary T cells co-treated with CXCR4- and CCR5-specific ZFNs as assayed by Surveyor™ nuclease assay. The top panel (R5) shows cells assayed for CCR5 modification while the bottom panel (X4) shows cells assayed for CXCR4 modification. Percent modification by non-homologous end joining (NHEJ) is shown at the bottom of each lane.

Fresh human CD4+ T cells isolated by negative selection were treated as described above in Example 4 except that a mixture of Ad5/F35×4 and Ad5/F35 R5 ZFNs were used (moi 600). Cells were analyzed for modification of both the CXCR4 gene sequence and the CCR5 sequence 14 days following transduction using the Surveyor™ assay described above. The results, shown in FIG. 11, indicate that both sequences were modified by the dual treatment. In some conditions, both target genes were modified (see lanes 6 and 7).

To assess cell growth, co-receptor disruption and HIV transcriptase activity following challenge, fresh human CD4+ T cells are isolated by negative selection and are seeded at a density of approximately $0.8 \times 10^6$ cells/ml and stimulated with antiCD3-antiCD28 coated magnetic beads at a 3:1 ratio in RPMI with 10% FCS, 1% Pen/Strep, and 100 units/mL IL-2. Cells are incubated for 18 hours and then transduced with Ad5/F35×4-ZFN (moi 600) and media volume will be doubled. Five days later beads are removed and cells are transduced with Ad5/F35 CCR5-ZFN (MOI 600). Suitable ation 20080159996. Approximately six days later, cells are CCR5 ZFNs are described, for example, in US Patent Application cre-stimulated with anti-CD3/antiCD28 coated magnetic beads and infected with HIV strains YU2, BK132, HxB, and R3A (100 ng p24). Cell growth, coreceptor disruption, and HIV reverse transcriptase activity are assessed every 2 days post-HIV infection.

What is claimed is:

1. A zinc finger protein comprising 4 zinc finger DNA-binding domains, wherein
   (i) each zinc finger DNA-binding domain binds to a 3 base pair target subsite;
   (ii) the zinc finger protein binds to a target site in a CXCR4 gene; and
   (iii) the target site is selected from the group consisting of SEQ ID NO:1, SEQ ID NO:6, SEQ ID NO:11, SEQ ID NO:16, SEQ ID NO:21 and SEQ ID NO:25.

2. A fusion protein comprising a zinc finger DNA-binding domain according to claim 1 and at least one cleavage domain or at least one cleavage half-domain.

3. The fusion protein of claim 2, wherein the cleavage half-domain is a wild-type FokI cleavage half-domain.

4. The fusion protein of claim 2, wherein the cleavage half-domain is an engineered FokI cleavage half-domain.

5. A polynucleotide encoding the zinc finger DNA-binding domain according to claim 1.

6. A gene delivery vector comprising the polynucleotide of claim 5.

7. The gene delivery vector of claim 6, wherein the vector comprises an adenovirus vector.

8. An isolated cell comprising a protein according to claim 1.

9. A method of inactivating an endogenous cellular CXCR4 gene in a cell, the method comprising:
   (a) introducing, into a cell, a first nucleic acid encoding a first polypeptide, wherein the first polypeptide comprises:
      (i) a zinc finger DNA-binding domain according to claim 1; and
      (ii) a cleavage domain; such that the polypeptide is expressed in the cell, whereby the polypeptide binds to the target site and cleaves the CXCR4 gene.

10. The method of claim 9, further comprising introducing a nucleic acid encoding a second polypeptide, wherein the second polypeptide comprises:
    (i) a zinc finger DNA-binding domain that is engineered to bind to a second target site in the CXCR4 gene; and
    (ii) a cleavage domain; such that the second polypeptide is expressed in the cell, whereby the first and second polypeptides bind to their respective target sites and cleave the CXCR4 gene.

11. The method of claim 9, wherein the first and second polypeptides are encoded by the same nucleic acid.

12. The method of claim 9, wherein the first and second polypeptides are encoded by different nucleic acids.

13. The method of claim 9, further comprising introducing a polynucleotide into the cell, wherein the polynucleotide comprises a first region of homology to sequences upstream of the double-strand break and a second region of homology to sequences downstream of the double-strand breaks.

14. The method of claim 9, wherein the nucleic acid is carried on a gene delivery vector.

15. The method of claim 14, wherein the gene delivery vector is an adenovirus vector.

16. The method of claim 15, wherein the adenovirus vector is an Ad5/F35 vector.

17. The method of claim 9, wherein the cell is selected from the group consisting of a hematopoietic stem cell, a T-cell, a macrophage, a dendritic cell and an antigen-presenting cell.

18. A method for treating or preventing HIV infection in a subject, the method comprising:
    (a) inactivating an endogenous cellular CXCR4 gene in a cell according to the method of claim 9, and
    (b) introducing the cell into the subject.

19. The method of claim 18, further comprising inactivating an endogenous CCR5 gene in the cell using a sequence encoding a nuclease prior to introducing the cell into the subject.

* * * * *